(12) United States Patent
Koster et al.

(10) Patent No.: US 11,173,137 B2
(45) Date of Patent: Nov. 16, 2021

(54) COMPOSITIONS AND METHODS TO MODULATE CHLORIDE ION CHANNEL ACTIVITY

(71) Applicant: The Board of Trustees of the Leland Stanford Junior University, Stanford, CA (US)

(72) Inventors: Anna K. Koster, Palo Alto, CA (US); Justin Du Bois, Palo Alto, CA (US); Merritt C. Maduke, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 16/449,021

(22) Filed: Jun. 21, 2019

(65) Prior Publication Data

US 2020/0016103 A1 Jan. 16, 2020

Related U.S. Application Data

(60) Provisional application No. 62/690,307, filed on Jun. 26, 2018.

(51) Int. Cl.
*A61K 31/196* (2006.01)
(52) U.S. Cl.
CPC .................. *A61K 31/196* (2013.01)
(58) Field of Classification Search
CPC .................................................. A61K 31/196
See application file for complete search history.

(56) References Cited

FOREIGN PATENT DOCUMENTS

WO   WO2012/033878   *   3/2012

OTHER PUBLICATIONS

Zhou et al. CAS: 137: 363076, 2002.*
Levitt et al. CAS: 135: 147436, 2001.*
Blanz et al. (2007) "Leukoencephalopathy upon Disruption of the Chloride Channel CIC-2" J Neurosci, 13;27(24):6581-9.
Edwards et al. (2010) "Photoreceptor Degeneration, Azoospermia, Leukoencephalopathy, and Abnormal RPE Cell Function in Mice Expressing an Early Stop Mutation in CLCN2" Invest Ophthalmol Vis Sci. 51(6): 3264-3272.
Scholl et al. (2018) "CLCN2 Chloride Channel Mutations in Familial Hyperaldosteronism Type II" Nat Genet, 50(3): 349-354.
Sun et al. (2016) "The CLC-2 Chloride Channel Modulates ECM Synthesis, Differentiation, and Migration of Human Conjunctival Fibroblasts via the PI3K/Akt Signaling Pathway" Int J Mol Sci; 17(6): 910.
Thiemann et al. "A Chloride Channel Widely Expressed in Epithelial and Non-Epithelial Cells", Nature 1992, 356 (6364), 57-60.

* cited by examiner

*Primary Examiner* — Rei Tsang Shiao
(74) *Attorney, Agent, or Firm* — Pamela J. Sherwood; Bozicevic, Field & Francis LLP

(57) ABSTRACT

Provided herein are small-molecules for use in modulating chloride ion channel (CLC) activity, particularly the activity of CLC-2, to elucidate the role of CLC-2 in disorders associated with CLC-2 malfunction, and to identify therapeutic leads for their treatment. Compositions and methods for modulating CLC activity are also provided. In certain aspects, the subject compounds and compositions are useful for imaging or channel pull-down studies.

6 Claims, 11 Drawing Sheets

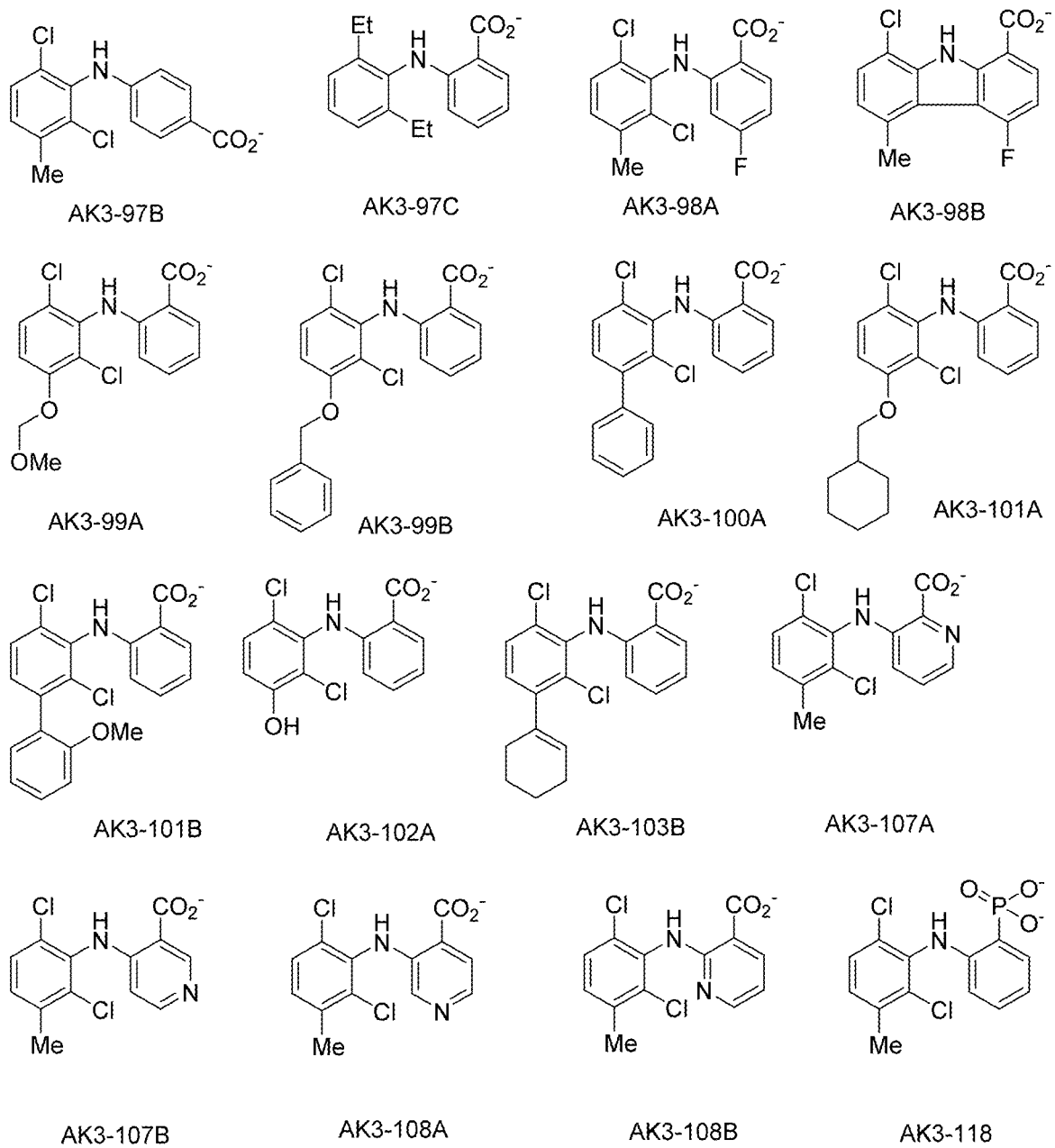
FIG. 6, continued

FIG. 6, continued
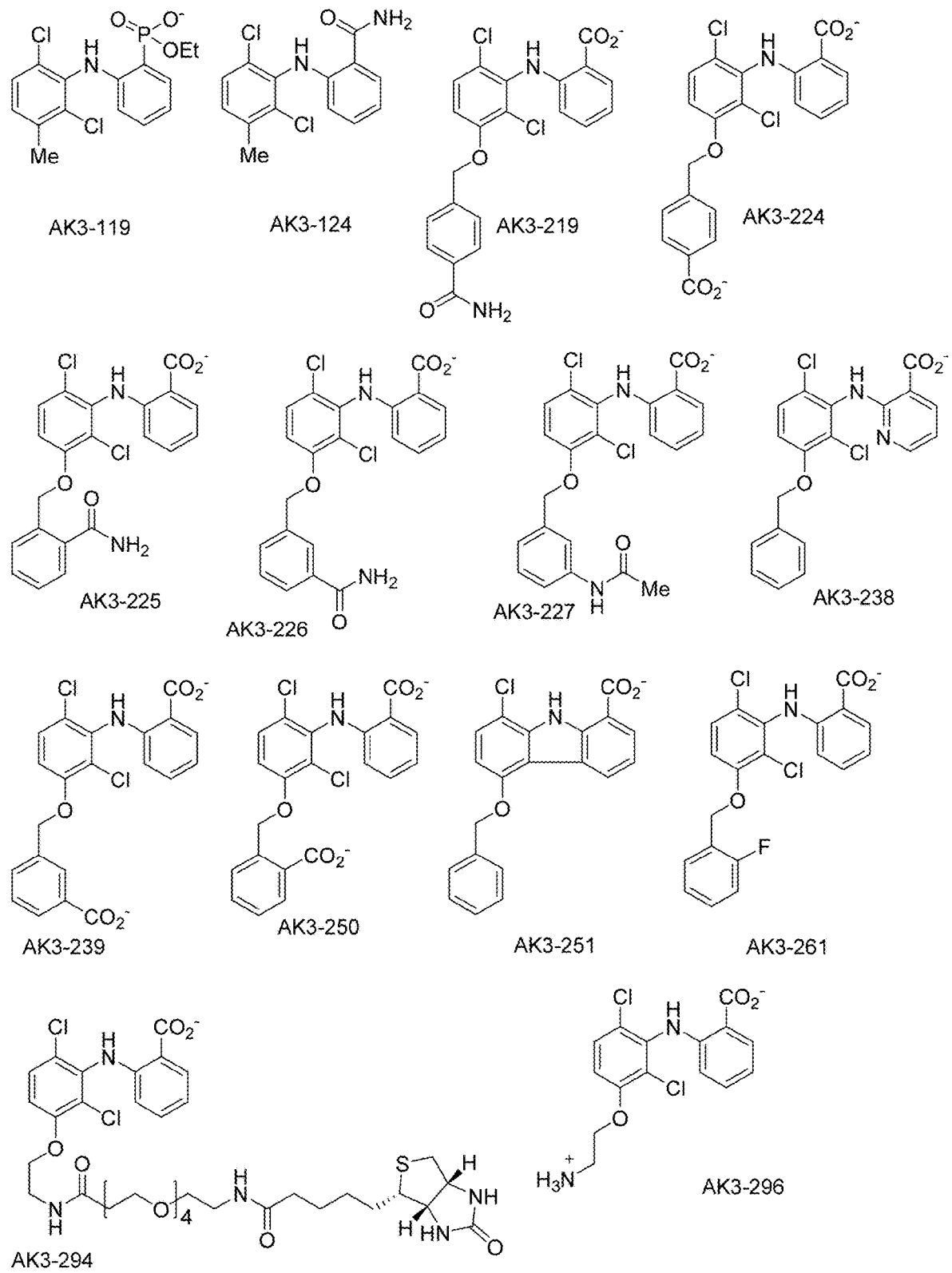

FIG. 6, continued
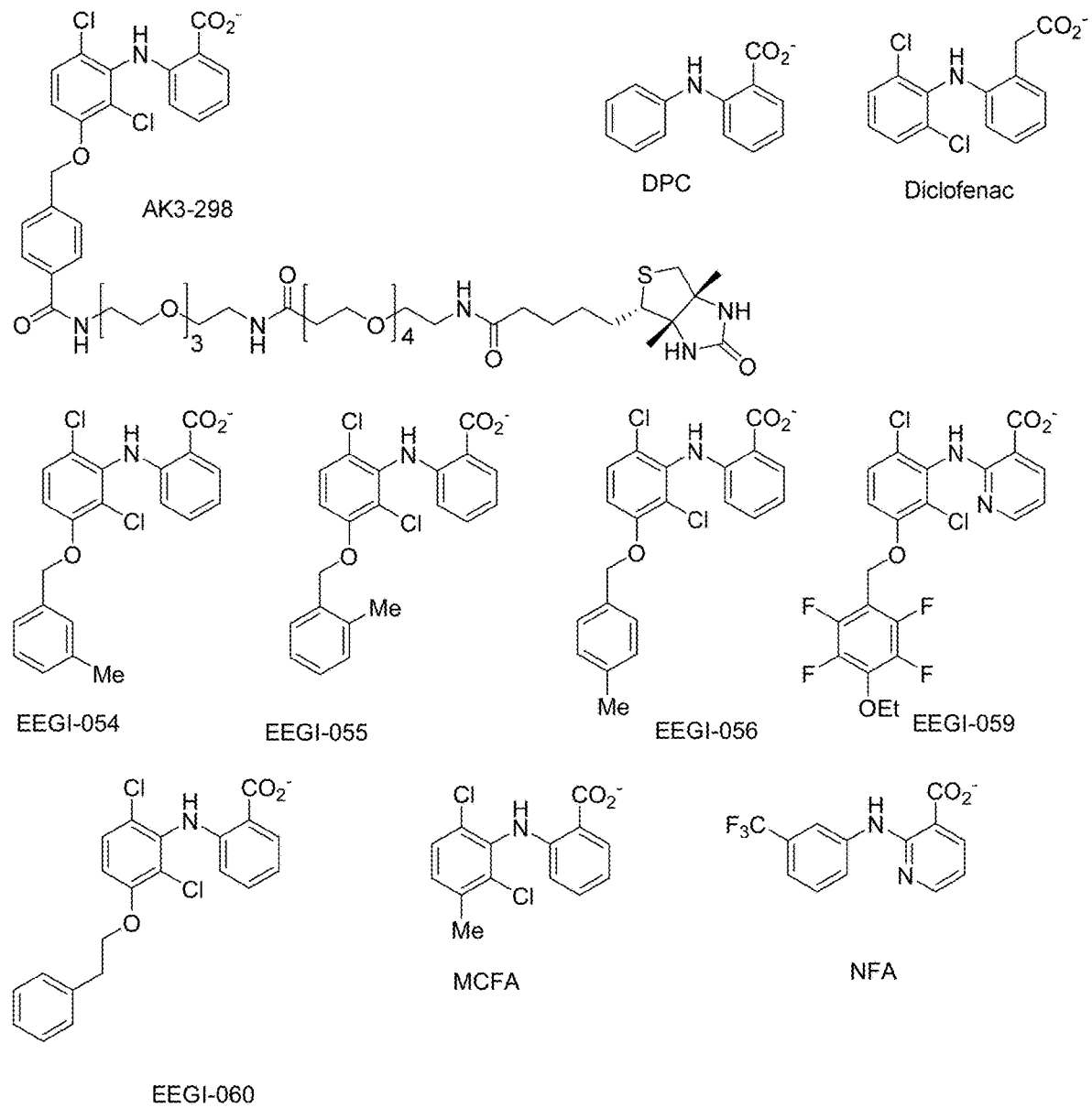

COMPOSITIONS AND METHODS TO MODULATE CHLORIDE ION CHANNEL ACTIVITY

CROSS-REFERENCE

This application claims the benefit of U.S. Provisional Patent Application No. 62/690,307, filed Jun. 26, 2018, which application is incorporated herein by reference in its entirety.

INTRODUCTION

The chloride ion channel (CLC) family of proteins is responsible for controlling the flux of chloride ions across cell membranes. CLCs function in transepithelial transport, electrical excitation of muscles and neurons, and homeostasis of cellular ion gradients. Of the nine mammalian CLC homologs, CLC-2 is the most abundant chloride channel expressed in the brain. It is present in the plasma membranes of neurons, astrocytes, and oligodendrocytes where its function remains largely unknown. Several studies have implicated CLC-2 defects as risk factors for human generalized epilepsies, although these claims remain controversial. The role of CLC-2 in glial cells, which are not electrically excitable, also remains unknown. Genetic knockouts of CLC-2 in neurons and glia display leukoencephalopathy (degeneration of white matter) with abnormal vacuolization between the myelin sheaths surrounding axons in the CNS. CLC-2 has also been identified as one of the primary chloride channels expressed in human glioma cells. Use of non-specific chloride channel blockers in this context renders glioma cells unable to migrate; however, the precise role of CLC-2 Cl⁻ secretion in brain tumor invasion is still a mystery.

Determining the underlying mechanisms of CLC-2 in disease has remained a challenge due to the absence of selective tools for reversibly modulating channel function in live cells. Design of homolog-specific, small-molecule inhibitors would enable studies interrogating the role of CLC-2 in neurons and glia while avoiding complications of compensatory changes in protein expression that accompany genetic knockout models. Unlike sodium, potassium, and calcium channels, no high-affinity, small-molecule inhibitors of CLC-2 are known. While several chloride channel inhibitors are reported in the literature, most of these are of low affinity (mid-µM to mM $IC_{50}$) and act non-specifically on many types of anion channels. The only known CLC-2-specific antagonist is a peptide toxin called GaTx2; however, the percent inhibition of CLC-2 function with GaTx2 saturates at 50%, thus severely limiting its use as a pharmacological probe. Given these limitations and that small-molecule inhibitors are much more amenable to synthetic manipulation, we chose to pursue a small-molecule, rational design approach to develop novel classes of CLC-2 inhibitors.

SUMMARY

Provided herein are small-molecules for use in modulating chloride ion channel (CLC) activity, particularly the activity of CLC-2. Compositions and methods for modulating CLC activity are also provided. In certain aspects, the subject compounds and compositions are useful for imaging, diagnostic tools, or channel pull-down studies.

CLC-2 is expressed in the majority of mammalian tissues and organs, but its physiological function remains only partially understood (Thiemann, A.; Gründer, S.; Pusch, M.; Jentsch, T. J. A Chloride Channel Widely Expressed in Epithelial and Non-Epithelial Cells. Nature 1992, 356 (6364), 57-60). Studies have implicated CLC-2 in disorders affecting the Central Nervous System (CNS) including, but not limited to, epilepsy, leukoencephalopathy (white-matter degeneration), and gliomas. Compounds of the present disclosure find use as tools to elucidate the details of CLC-2 function in these diseases, to identify therapeutic leads for their diagnosis and treatment, and also to serve as therapeutic leads, themselves. CLC-2 malfunction has also been linked to diseases of the eye (retinal degeneration (Blanz et al. J Neurosci. 2007 Jun. 13; 27(24):6581-9), post-operative scarring after glaucoma surgery (Sun et al. Int J Mol Sci. 2016 June; 17(6): 910)), reproductive system (testes degeneration (Blanz et al. J Neurosci. 2007 Jun. 13; 27(24):6581-9), azoospermia (Edwards et al. Invest Ophthalmol Vis Sci. 2010 June; 51(6): 3264-3272)), and kidneys (primary aldosteronism/hypertension (Scholl et al. Nat Genet. 2018 March; 50(3): 349-354)). Specific chemical modulators (activators and inhibitors) of CLC-2 can enable investigation of channel function in these and other systems, and can serve as novel therapeutic leads and medical diagnostic tools.

BRIEF DESCRIPTION OF THE FIGURES

FIG. 8, panel B depicts a summary graph showing the mean inhibition of CLC-1 and CLC-2 for exemplary compounds FA44, FA26 (also referred to herein as AK3-99B), FA35 (also referred to herein as AK3-108B) and meclofenamate (MCFA).

DEFINITIONS

Figure 1:
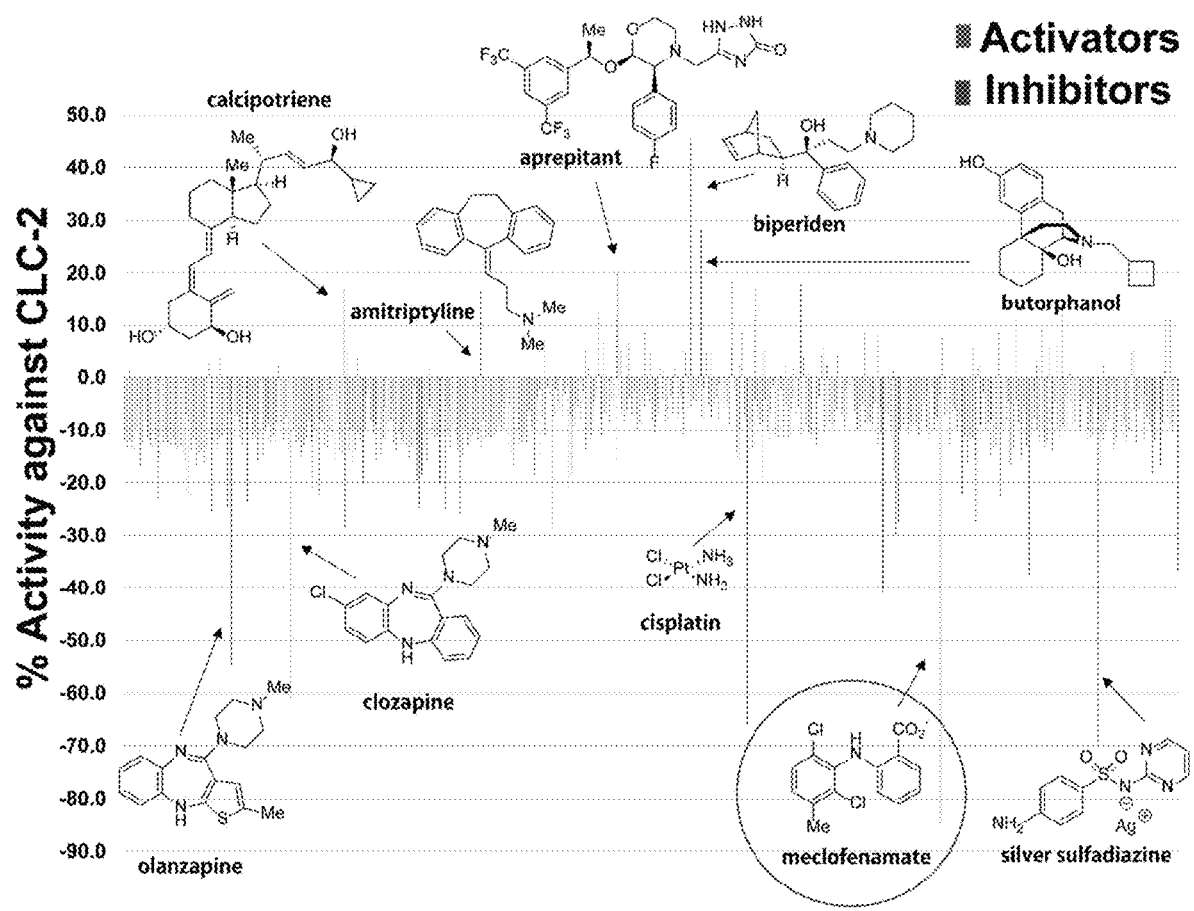
FIG. 1 provides results of an 800-compound screen against human CLC-2 expressed in CHO cells, using automated patch-clamp electrophysiology.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112. In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure and are not meant to be limiting in any fashion.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease (e.g., reduction in viral titers).

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general, a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a mono- radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocylooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—CH$_2$—), ethylene (—CH$_2$CH$_2$—), propylene (—CH$_2$CH$_2$CH$_2$—), 2-methylpropylene (—CH$_2$—CH(CH$_3$)—CH$_2$—), hexylene (—(CH$_2$)$_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

"Carboxyl," "carboxy" or "carboxylate" refers to —CO$_2$H or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO— alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO2), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO$_2$-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$ M$^+$, —NR$^{70}$CO$_2$R$^{70}$, —NR$^{70}$C(S)OR$^{70}$, —NR$_{70}$C(O)NR$_{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$ (M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —CO(O)R$^{70}$, —CO(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

As used here, the term "modulating chloride ion channel (CLC) activity" refers to the modulation (e.g., inhibition or diminishment) of CLC activity in a given subject and includes states of reduced or absent CLC activity.

Definitions of other terms and concepts appear throughout the detailed description.

DETAILED DESCRIPTION

As summarized above, aspects of the disclosure includes small-molecules for use in modulating chloride ion channel (CLC) activity, particularly the activity of CLC-2. Compositions and methods for modulating CLC activity are also provided. In certain aspects, methods are provided for modulating chloride ion channel (CLC) activity of CLC-2, to elucidate the role of CLC-2 in disorders affecting the Central Nervous System including, but not limited to, epilepsy, leukoencephalopathy, and gliomas, and to identify therapeutic leads for their treatment. In certain aspects, the subject compounds and compositions are useful for imaging, use as diagnostic tools, or channel pull-down studies.

Compounds

As summarized above, aspects of the disclosure includes compounds for use in modulating CLC activity, e.g., small-molecule CLC-2 inhibitors for modulating CLC-2 activity. The compounds disclosed herein are based on a meclofenamate core structure. Meclofenamate (MCFA) has the following structure:

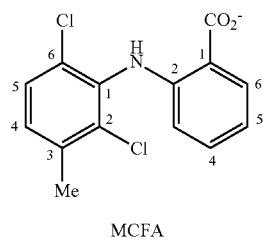

MCFA

The compounds can be a compound based on MCFA which is substituted at the 3-position of the Western ring. In certain cases, the 3-position substituent is an O-benzyl group, or a substituted O-benzyl group (e.g., as described herein). In certain cases, the compounds include an anionic group in the Eastern ring. In certain cases, the Eastern ring includes one or more nitrogen atoms. Exemplary compounds find use in modulating CLC-2 activity. Exemplary compounds are set forth in the following structures and formula.

In certain embodiments, the subject compound is described by formula (I):

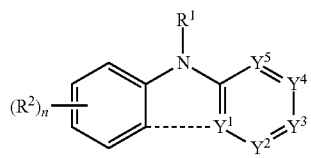

(I)

wherein:
--- is absent, or a bond;
$R^1$ is selected from hydrogen, alkyl, substituted alkyl, and -L-Z;
$R^2$ is selected from halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;
$Y^1$ is selected from N and $CR^3$, wherein $R^3$ is selected from hydrogen, carboxyl, substituted carboxyl, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;
or $Y^1$ is C when --- is a bond;
$Y^2$-$Y^5$ are each independently selected from N and $CR^3$, wherein $R^3$ is selected from hydrogen, carboxyl, substituted carboxyl, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker (e.g., PEG, alkyl chain etc.);

Z is selected from a chemoselective group, an affinity tag, an isotopic label and a fluorescent label; and n is an integer from 0 to 5, or a pharmaceutically acceptable salt or a solvate thereof.

In certain cases of a compound of formula (I), --- is a bond, e.g., the compound of formula (I) is a carbazole. For example, the compound of formula (I) may be described by one of the following structures:

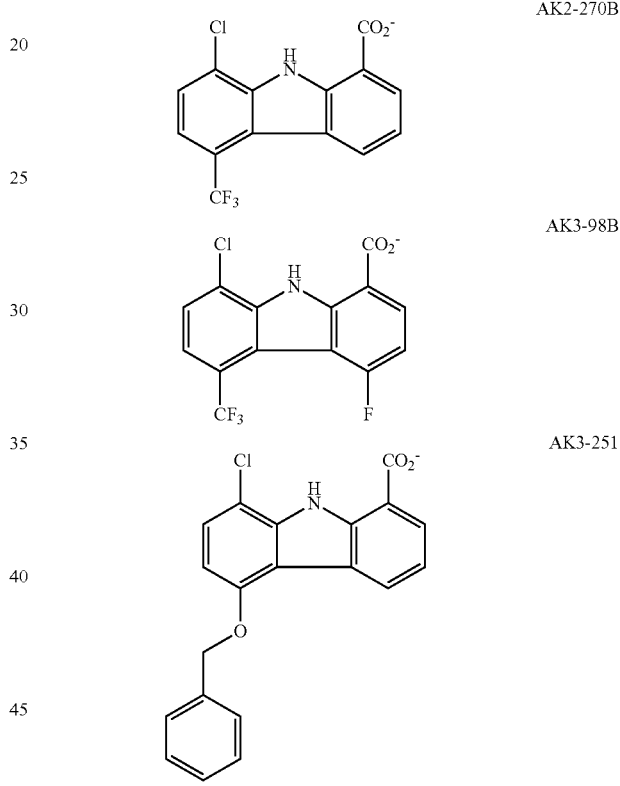

In certain cases of a compound of formula (I), --- is absent. For example, the compound of formula (I) may be described by any of the structures in FIG. 6, other than AK2-270B, AK3-93B or AK3-251.

In certain cases of a compound of formula (I), one or more of $Y^1$-$Y^5$ is N. In certain cases, one of $Y^1$-$Y^5$ is N, e.g., the eastern ring is pyridyl or substituted pyridyl. In certain cases, two of $Y^1$-$Y^5$ are N, e.g., the eastern ring is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl.

In certain cases of a compound of formula (I), one or more of $Y^1$-$Y^5$ is $CR^3$. In certain cases at least one $R^3$ group is an anionic group. As used herein, "anionic group" includes bioisosteres of the said anionic groups. Non-limiting anionic groups of interest include a carboxylate, a phosphoryl, a sulfate, a tetrazole, and an amido moiety. In certain cases, the anionic group is a carboxylate. In certain cases, the anionic group is a phosphoryl. In certain cases, the anionic group is a sulfate. In certain cases, the anionic group is a tetrazole moiety. In certain cases, the anionic group is an amido moiety. In certain embodiments, $R^3$ is an isostere (e.g., bioisostere) of a carboxyl group. By "isostere" or "bioisostere" is meant a derivative of an active compound (e.g., a therapeutically effective active compound), where the derivative produces substantially similar biological effects in vivo as compared to the active compound. In some embodiments, compounds of the present disclosure include a tetrazolone or substituted tetrazolone and are isosteres (e.g., bioisosteres) of an active compound that includes a carboxyl group.

In certain cases of a compound of formula (I), n is 1, 2, 3, 4 or 5, such that the compound includes one or more $R^2$ groups. In certain cases, one or more $R^2$ is halogen, e.g., Br, Cl, F, or I. In certain cases, one or more $R^2$ groups is chloride. In certain cases, two $R^2$ groups are chloride. In certain cases, the $R^2$ groups are at the 2 and 6 positions of the western ring. In certain cases, one or more $R^2$ is alkyl, e.g. methyl, ethyl, propyl, butyl, pentyl, hexyl etc. In certain cases, one or more $R^2$ groups is methyl. In certain cases, one $R^2$ group is at the 3 position of the western ring. In certain cases, the $R^2$ group at the 3 position is selected from halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z. In certain cases, the $R^2$ group at the 3 position is halogen. In certain cases, the $R^2$ group at the 3 position is alkyl. In certain cases, the $R^2$ group at the 3-position is alkenyl. In certain cases, the $R^2$ group at the 3-position is aryl. In certain cases, the $R^2$ group at the 3 position is alkoxy. In certain cases, the $R^2$ group at the 3-position is substituted alkoxy. In certain cases, the $R^2$ group at the 3-position is O-benzyl or substituted O-benzyl.

In certain In certain embodiments, the subject compound is described by formula (II):

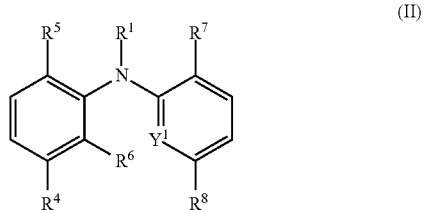

wherein:

$R^1$ is selected from hydrogen, alkyl, substituted alkyl, and -L-Z;

$R^4$ is selected from halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

$R^5$ and $R^6$ are each independently selected from halogen, alkyl, and substituted alkyl;

$Y^1$ is selected from N and CH;

$R^7$ is an anionic group;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker (e.g., PEG, alkyl chain etc.);

Z is selected from a chemoselective group, an affinity tag, an isotopic label and a fluorescent label;

or a pharmaceutically acceptable salt or a solvate thereof.

In certain embodiments of formula (II), $R^4$ is alkyl or substituted alkyl. In certain cases, $R^4$ is alkenyl, or substituted alkenyl. In some cases, $R^4$ comprises an alkynyl or a substituted alkynyl. In certain cases, $R^4$ comprises an azide moiety. In certain cases, $R^4$ is hydroxyl. In certain cases, $R^4$ is aryl or substituted aryl. In certain cases, $R^4$ is cycloalkyl or substituted cycloalkyl. In certain cases, $R^4$ is alkoxy or substituted alkoxy. In certain cases, $R^4$ is O-benzyl or substituted O-benzyl. In certain cases, $R^4$ is -L-Z.

In certain embodiments of formula (II), $R^5$ and $R^6$ are each halogen, e.g., Cl, Br, I, F. In some cases, $R^5$ and $R^6$ are both chloride. In certain cases, $R^5$ and $R^6$ are both fluoride. In certain embodiments of formula (II), $R^5$ and $R^6$ are both alkyl. In certain cases, both $R^5$ and $R^6$ are lower alkyl, e.g., methyl, ethyl, propyl, butyl, pentyl or hexyl.

In certain embodiments of formula (II), $R^8$ is hydrogen. In certain cases, $R^8$ is halogen. In certain cases, $R^8$ is alkyl or substituted alkyl. In certain cases, $R^8$ is alkenyl, or substituted alkenyl. In some cases, $R^8$ comprises an alkynyl or a substituted alkynyl. In certain cases, $R^8$ comprises an azide moiety. In certain cases, $R^8$ is hydroxyl. In certain cases, $R^8$ is aryl or substituted aryl. In certain cases, $R^8$ is cycloalkyl or substituted cycloalkyl. In certain cases, $R^8$ is alkoxy or substituted alkoxy. In certain cases, $R^8$ is -L-Z.

In certain embodiments of formula (II), $R^7$ is selected from a carboxylate, a phosphoryl, a sulfate, a tetrazole, and an amido. In certain cases, $R^7$ is a carboxylate. In certain cases, $R^7$ is a phosphoryl. In certain cases, $R^7$ is a sulfate. In certain cases, $R^7$ is a tetrazole. In certain cases, $R^7$ is an amido moiety.

In certain embodiments of any one of formulae (I) or (II), $R^1$ is hydrogen. In certain embodiments of formulae (I) or (II), $R^1$ is alkyl or substituted alkyl. In certain embodiments of formulae (I) or (II), $R^1$ is -L-Z.

In certain In certain embodiments, the subject compound is described by formula (III):

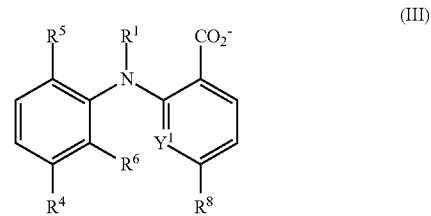

wherein:

$R^4$ is selected from alkyl, substituted alkyl, alkenyl, substituted alkenyl, alkynyl, substituted alkynyl, azide, hydroxyl, aryl, substituted aryl, cycloalkyl, substituted cycloalkyl, alkoxy, substituted alkoxy, and -L-Z;

$R^5$ and $R^6$ are each independently selected from halogen, alkyl, substituted alkyl;

$Y^1$ is selected from N and CH;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker (e.g., PEG, alkyl chain etc.);

Z is selected from a chemoselective group, an affinity tag an isotopic label and a fluorescent label;

or a pharmaceutically acceptable salt or a solvate thereof.

In certain embodiments of formula (III), $R^4$ is alkyl or substituted alkyl. In certain cases, $R^4$ is alkenyl, or substituted alkenyl. In some cases, $R^4$ comprises an alkynyl or a substituted alkynyl. In certain cases, $R^4$ comprises an azide moiety. In certain cases, $R^4$ is hydroxyl. In certain cases, $R^4$ is aryl or substituted aryl. In certain cases, $R^4$ is cycloalkyl or substituted cycloalkyl. In certain cases, $R^4$ is alkoxy or substituted alkoxy. In certain cases, $R^4$ is O-benzyl or substituted O-benzyl. In certain cases, $R^4$ is -L-Z.

In certain embodiments of formula (III), $R^5$ and $R^6$ are each halogen, e.g., Cl, Br, I, F. In some cases, $R^5$ and $R^6$ are both chloride. In certain cases, $R^5$ and $R^6$ are both fluoride. In certain embodiments of formula (III), $R^5$ and $R^6$ are both alkyl. In certain cases, both $R^5$ and $R^6$ are lower alkyl, e.g., methyl, ethyl, propyl, butyl, pentyl or hexyl.

In certain embodiments of formula (III), $R^8$ is hydrogen. In certain cases, $R^8$ is halogen. In certain cases, $R^8$ is alkyl or substituted alkyl. In certain cases, $R^8$ is alkenyl, or substituted alkenyl. In some cases, $R^8$ comprises an alkynyl or a substituted alkynyl. In certain cases, $R^8$ comprises an azide moiety. In certain cases, $R^8$ is hydroxyl. In certain cases, $R^8$ is aryl or substituted aryl. In certain cases, $R^8$ is cycloalkyl or substituted cycloalkyl. In certain cases, $R^8$ is alkoxy or substituted alkoxy. In certain cases, $R^8$ is -L-Z.

In certain embodiments of any one of formulae (I)-(III), the compound may comprise the group -L-Z, wherein L is an optional linker and Z is selected from a chemoselective group, an affinity tag an isotopic label and a fluorescent label.

In certain embodiments of any one of formulae (I)-(III) comprising the group -L-Z, the compound includes a linker (e.g., as described herein). Suitable linkers include, but are not limited to, a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, a nitro, a PEG, and a peptide linker.

Exemplary linkers for use in linking the Z group to the subject compound of any one of formulae (I)-(III) will in some embodiments include a PEG linker. As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a functional group (e.g., as described herein). Any convenient linking groups may be utilized at the terminal of a PEG to connect the group to a moiety of interest including but not limited to, alkyl, aryl, hydroxyl, amino, acyl, acyloxy, carboxyl ester and amido terminal and/or substituent groups. In certain instances, the linker includes more than 1 PEG unit, such as 2, 3, 4, 5, 6, 7, 8, 9 or 10 PEG units. In certain instances, the linker includes less than 10 PEG units, such as 9, 8, 7, 6, 5, 4, 3, 2 or 1 PEG unit. In certain cases, linker is composed of 4 or fewer PEG units.

In certain embodiments of any one of formulae (I)-(III) comprising the group -L-Z, Z is a chemoselective group. As used herein, the terms "chemoselective group", "chemoselective functional group" and "chemoselective tag" are used interchangeably and refer to chemoselective reactive groups that are capable of selectively reacting with a compatible chemoselective functional group to form a covalent bond, or to one or more such chemoselective reactive group and a linking group. Hence, in some cases, the chemoselective group includes one or more chemoselective reactive groups and linking group that links one or more chemoselective groups to another group. In some cases, the chemoselective reactive group is capable of selectively reacting with a compatible chemoselective functional group to form a covalent bond after activation of one or more functional groups.

Chemoselective functional groups of interest include, but are not limited to, amines and carboxylic acids or active esters thereof, amines and isocyanates, amines and isothiocyanates, amines and N-hydroxysuccinimide (NHS) esters, amines and aldehydes (e.g. glyoxals), thiols and maleimides, thiols and iodoacetamides, carboxylic acids and thiols, tetrazines and alkenes, as well as groups that can react with one another via Click chemistry, e.g., azide and alkyne groups, tetrazine, transcyclooctene, azides and phosphines (e.g. Staudinger ligation), dienes and dieneophiles, sulfur(VI) fluoride exchange chemistry (SuFEX), sulfonyl fluoride, hydrazido, hydrazine, aldehyde, ketone, azido, alkyne, phosphine, epoxide, and the like. See, FIG. 5, for an example of an exemplary compound used in Click chemistry. Additional chemoselective groups are described by Hermanson, Bioconjugate Techniques, Third Edition, Academic Press, 2013.

In certain embodiments of any one of formulae (I)-(III) comprising the group -L-Z, Z is an affinity tag. As used herein, the term "affinity tag" refers to a member of a specific binding pair, i.e. two molecules where one of the molecules through chemical or physical means specifically binds to the other molecule. The complementary member of the affinity tag may be immobilized (e.g., to a chromatography support, a bead or a planar surface) to produce an affinity chromatography support that specifically binds the affinity tag. Tagging a compound of interest with an affinity tag allows the compound to be separated from a mixture of untagged compounds by affinity, e.g., using affinity chromatography. Examples of specific binding pairs include biotin and streptavidin (or avidin), and antigen and antibody, although binding pairs, e.g., nucleic acid hybrids, polyhistidine and nickel, and azido and alkynyl (e.g., cyclooctynyl) or phosphino groups are also envisioned. The specific binding pairs may include analogs, derivatives and fragments of the original specific binding members. See, FIG. 5, for an example of an exemplary compound including a biotin affinity tag.

As used herein, the term "biotin moiety" or "biotin" refers to an affinity tag that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least 10-8M. A biotin moiety may also include a linker, e.g., -LC-biotin, -LC-LC-Biotin, -SLC-Biotin or -PEGn1-Biotin where n1 is 3-12.

In certain embodiments of any one of formulae (I)-(III) comprising the group -L-Z, Z is an isotopic label. Exemplary isotopic labels may comprise radioactive isotopes (e.g., gamma-emitters, beta-emitters, and positron-emitters) or non-radioactive isotopes (e.g., stable trace isotopes), such as, but not limited to, $^{3}H$, $^{2}H$, $^{120}I$, $^{123}I$, $^{124}I$, $^{125}I$, $^{131}I$, $^{35}S$, $^{11}C$, $^{13}C$, $^{14}C$, $^{32}P$, $^{15}N$, $^{13}N$, $^{110}In$, $^{111}In$, $^{177}Lu$, $^{18}F$, $^{52}Fe$, $^{62}Cu$, $^{64}Cu$, $^{67}Cu$, $^{67}Ga$, $^{68}Ga$, $^{86}Y$, $^{90}Y$, $^{89}Zr$, $^{94}mTc$, $^{94}Tc$, $^{99}mTc$, $^{154}Gd$, $^{155}Gd$, $^{156}Gd$, $^{157}Gd$, $^{158}Gd$, $^{15}O$, $^{186}Re$, $^{188}Re$, $^{51}M$, $^{52}Mn$, $^{55}Co$, $^{72}As$, $^{75}Br$, $^{76}Br$, $^{82}mRb$, and $^{83}Sr$. Exemplary compounds comprising $^{18}F$ or $^{11}C$ can be used in PET imaging. For example, a subject compound can be isotopically labeled with $^{18}F$ or $^{11}C$ or conjugated to $^{18}F$ or $^{11}C$-labeled compounds for use in positron emission tomography (PET) imaging.

In certain embodiments of any one of formulae (I)-(III) comprising the group -L-Z, Z is a fluorescent label. The term "fluorescent label" refers to a substance or a portion thereof which is capable of exhibiting fluorescence in the detectable range. Particular examples of labels which may be used in the practice of the disclosure include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2',4',5',7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), 3-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP).

Figure 6:
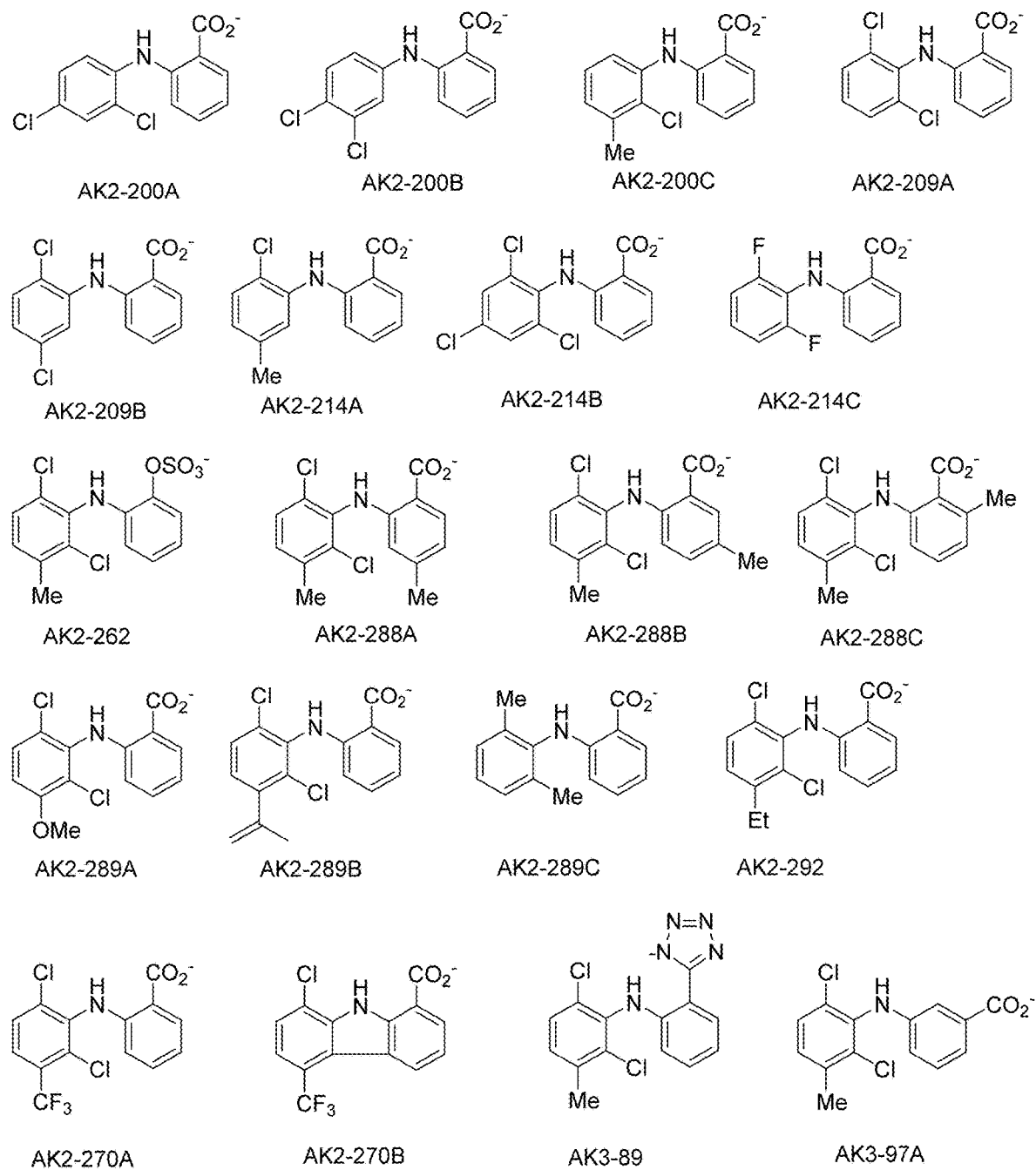
FIG. 6 shows next-generation CLC-2 probes for which $IC_{50}$ values were obtained, as explained and illustrated in Table 1.

In certain embodiments, the compound of any one of formulae (I)-(III) is described by a compound of FIG. 6.

In certain embodiments, the compound is not meclofenamate:

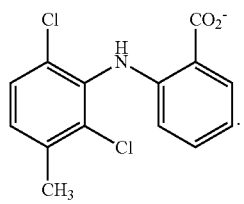

In certain embodiments, the compound is a compound selected from:

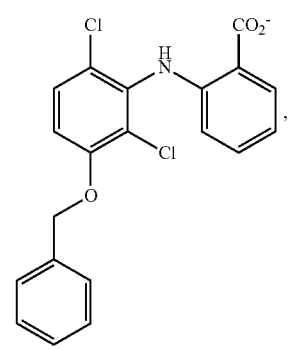
AK3-99B

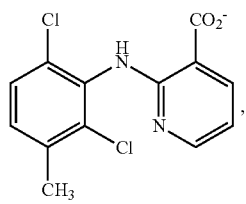
AK3-108B

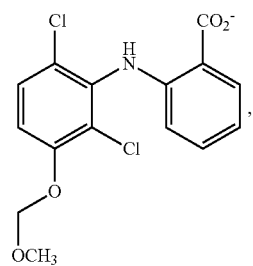
AK3-99A

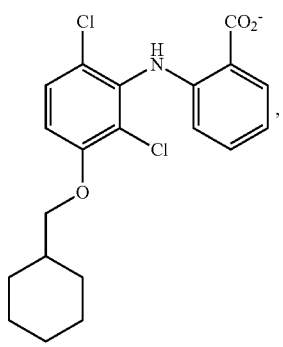
AK3-101A

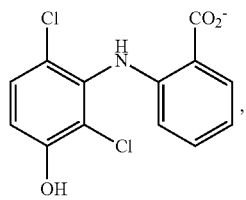
AK3-102A

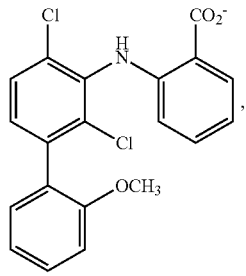
AK3-101B

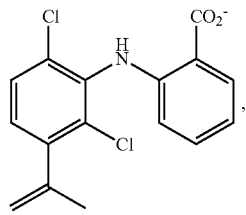
AK2-289B

-continued

In certain embodiments, the compound is selected from:

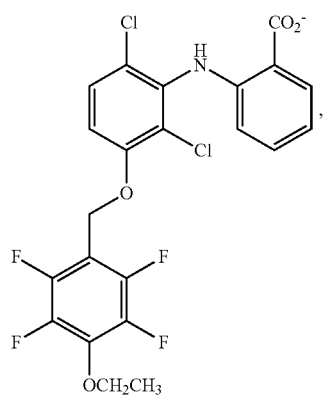
EEFI-059
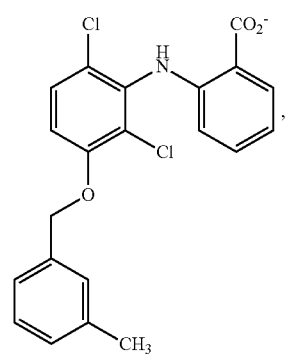
EEGI-055
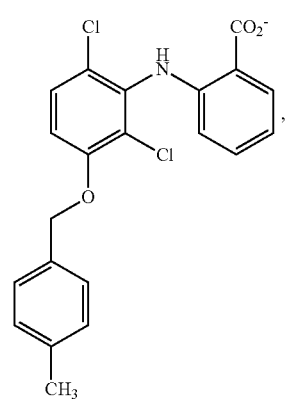
EEGI-054
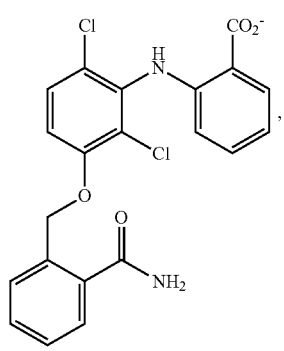
AK3-225
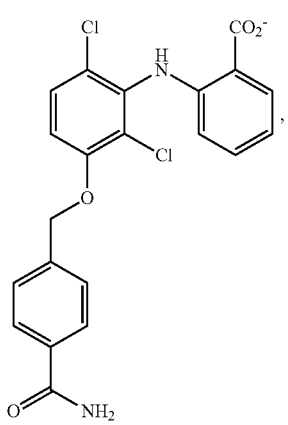
AK3-219
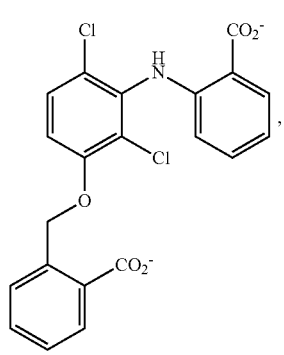
AK3-250
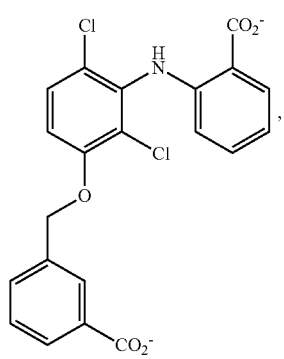
AK3-239
EEGI-056

AK3-224

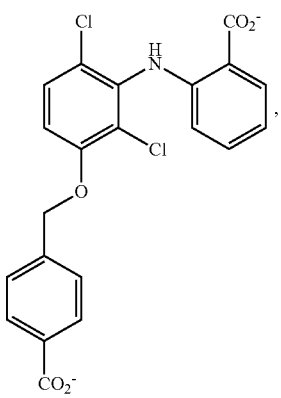

AK3-226

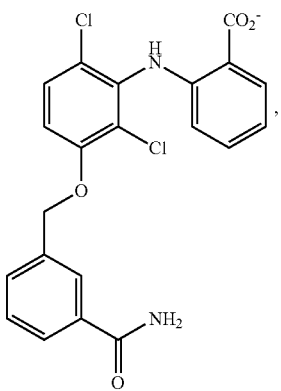

AK3-227

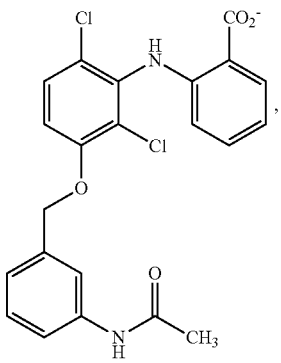

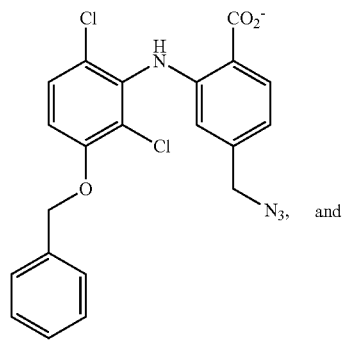 and

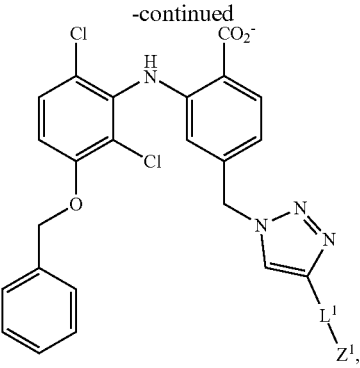

wherein:

L¹ is a PEG linker,

Z¹ is a biotin moiety.

In certain embodiments, the compound is AK3-238 (also referred to herein as FA44).

In certain embodiments, the compound is AK3-99B (also referred to herein as FA26).

Compositions

Aspects of the invention also include compositions, e.g., compositions including a subject compound (e.g., as described herein) formulated using any convenient excipients, reagents and methods. In one embodiment, there is provided a composition comprising an amount of a meclofenamate derivative effective to modulate chloride ion channel (CLC) function. In some cases, the CLC is CLC-2. In certain cases, the subject composition modulates CLC-2 function outside of a living organism. In certain cases, the subject composition modulates CLC-2 function in a living organism.

In certain embodiments, the composition comprises a compound of any one of formulae (I)-(III) (e.g., as described herein), or any one of the compounds shown in FIG. 6.

In certain embodiments, the composition includes a compound selected from:

AK3-99B

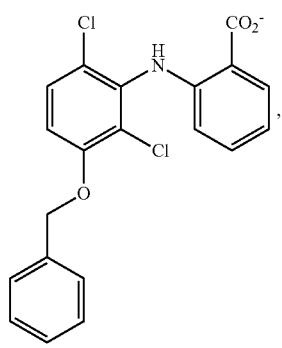

AK3-108B

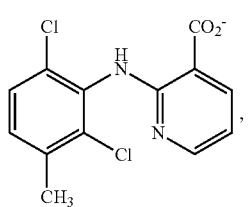

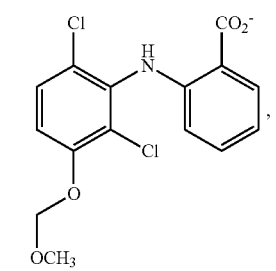
AK3-99A
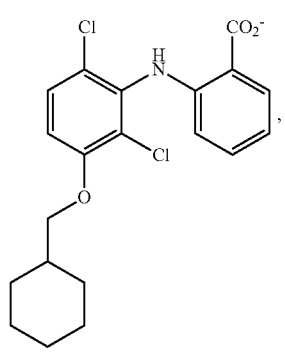
AK3-101A
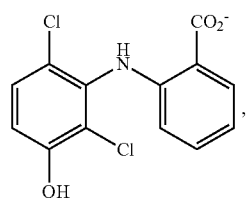
AK3-102A
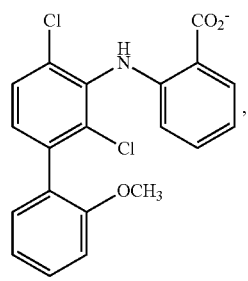
AK3-101B
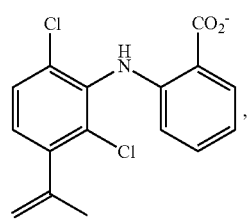
AK2-289B
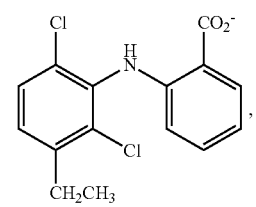
AK2-292
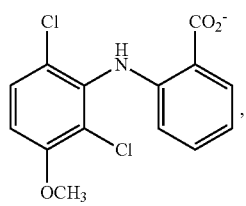
AK2-289A
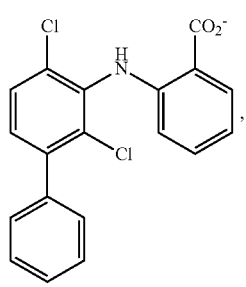
AK3-100A
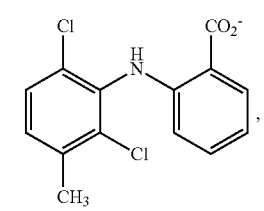
MCFA
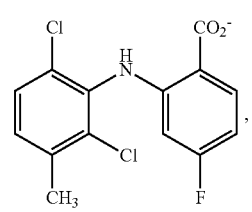
AK3-98A
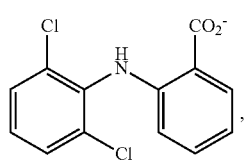
AK2-209A
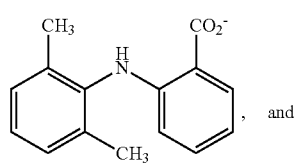
AK2-289C, and
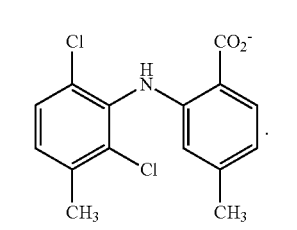
AK2-288A In certain embodiments, the composition comprises a compound is selected from:
AK3-99B
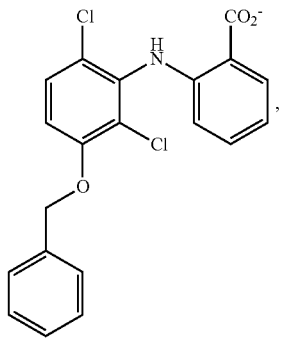
AK3-238
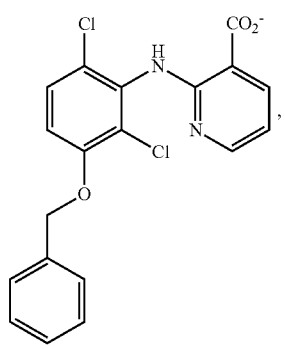
EEGI-060
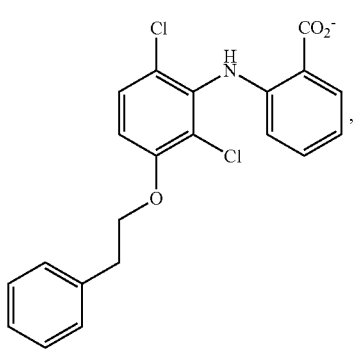
AK3-261
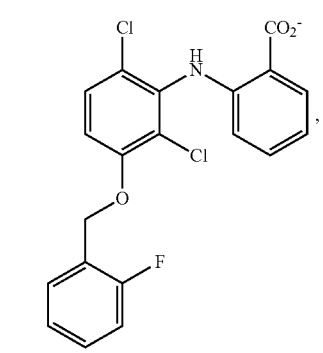
EEFI-059
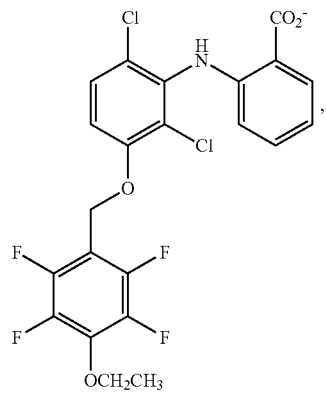
EEGI-055
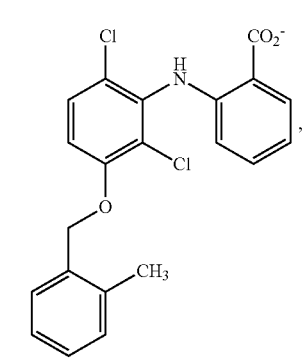
EEGI-054
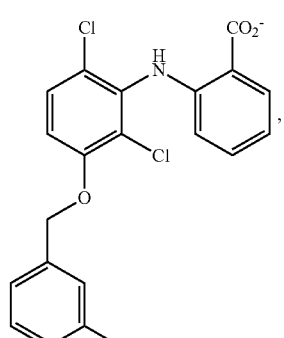
EEGI-056
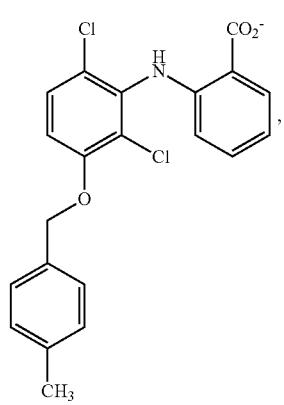

AK3-225 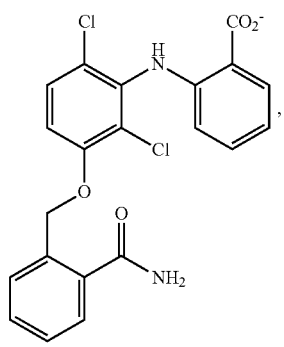
AK3-219 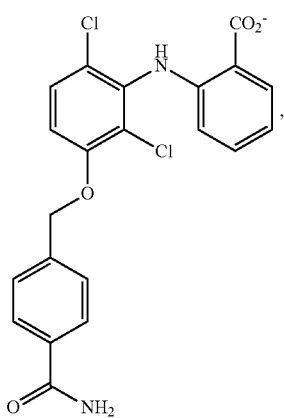
AK3-250 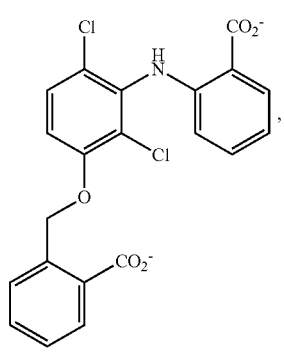
AK3-239 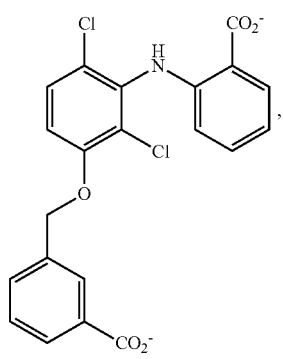
AK3-224 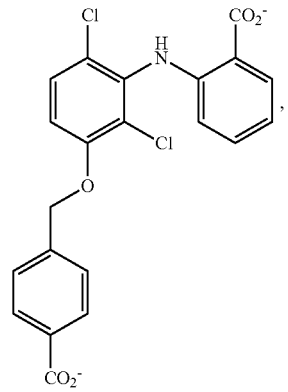
AK3-226 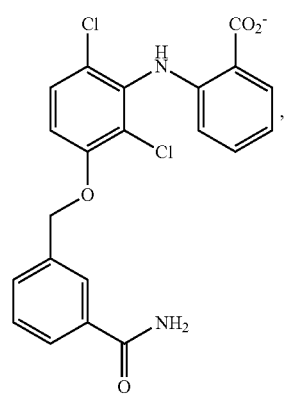
AK3-227 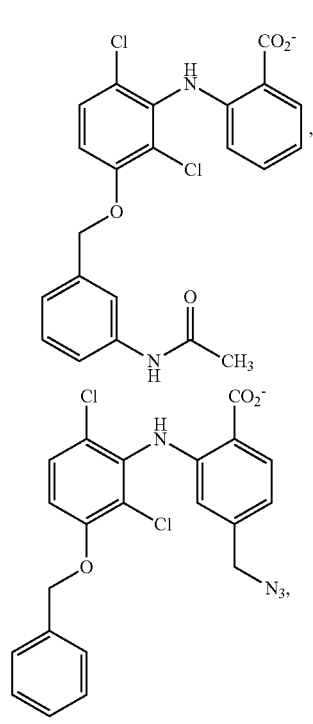
and -continued

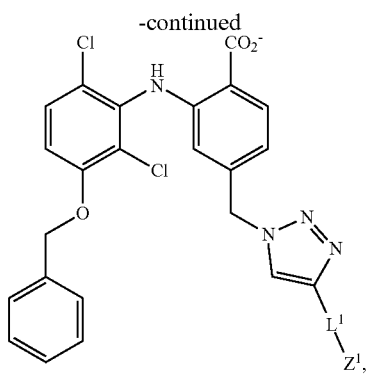

wherein:
L¹ is a PEG linker,
Z¹ is a biotin moiety.

In certain embodiments, the composition comprises the compound AK3-238 (also referred to herein as FA44).

In certain embodiments, the composition comprises the compound AK3-99B (also referred to herein as FA26).

Compositions can be provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release. In some embodiments, the subject compound is formulated for depot release.

In some embodiments of the present invention, a pharmaceutical composition is provided, comprising, or consisting essentially of, a compound of the present invention, or a pharmaceutically acceptable salt, isomer, tautomer or prodrug thereof, and further comprising one or more additional active agents of interest. Any convenient active agents may find use in the present disclosure. For example, including but not limited to, an active agent used for treating disorders affecting the Central Nervous System (CNS) including, but not limited to, epilepsy, leukoencephalopathy (white-matter degeneration), and gliomas; an active agent for treating diseases of the eye (retinal degeneration); an active agent for treating post-operative scarring after glaucoma surgery; an active agent for treating a disorder of the reproductive system (e.g., testes degeneration, azoospermia); and active agents for treating primary aldosteronism/hypertension.

The subject compound, as well as any additional therapeutic agents for combination therapies, can be administered orally, subcutaneously, intramuscularly, intranasally, parenterally, or other route. The subject compound and second agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ. In certain cases, the therapeutic agents can be administered intranasally.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Methods

As summarized above, provided herein are methods for modulating CLC activity, particularly CLC-2 chloride channel activity.

In one embodiment, there is provided a method for modulating CLC-2 chloride channel activity in a subject suffering from a disease related to CLC-2 malfunction, comprising administering to the subject an effective amount of a subject compound (e.g. a meclofenamate derivative as described herein). In certain embodiments, the disease is selected from a disorder affecting the Central Nervous System (CNS), diseases of the eye, post-operative scarring after glaucoma surgery, reproductive system disorders, and kidney disorders.

In certain embodiments, there is provided a method for modulating CLC-2 chloride channel activity in a subject suffering from a central nervous disorder, comprising administering to the subject an effective amount of a meclofenamate derivative (e.g. a compound, or composition as described herein).

Non-limiting examples of disorders affecting the CNS, include epilepsy, leukoencephalopathy (white-matter degeneration), and gliomas. In certain cases, the subject method is a method of modulating CLC-2 activity in a subject suffering from epilepsy. In certain cases, the subject method is a method of modulating CLC-2 activity in a subject suffering from leukoencephalopathy (white-matter degeneration). In certain cases, the subject method is a method of modulating CLC-2 activity in a subject having a glioma.

In certain cases, the subject method is a method of modulating CLC-2 activity in a subject suffering from a disease of the eye, comprising administering to the subject an effective amount of a meclofenamate derivative (e.g. a compound, or composition as described herein). In certain cases, the disease of the eye is retinal degeneration.

In certain cases, the subject method is a method of modulating CLC-2 activity in a subject suffering from post-operative scarring after glaucoma surgery, comprising administering to the subject an effective amount of a meclofenamate derivative (e.g. a compound, or composition as described herein).

In certain cases, the subject method is a method of modulating CLC-2 activity in a subject suffering from a reproductive system disorder, comprising administering to the subject an effective amount of a meclofenamate derivative (e.g. a compound, or composition as described herein). In certain cases, the reproductive system disorder is testes degeneration, or azoospermia.

In certain cases, the subject method is a method of modulating CLC-2 activity in a subject suffering from a kidney disorder, comprising administering to the subject an effective amount of a meclofenamate derivative (e.g. a compound, or composition as described herein). In certain cases, the kidney disorder is primary aldosteronism or hypertension.

Modulating CLC-2 Chloride Channel Activity

Aspects of the subject methods include modulating CLC-2 activity. By modulating CLC-2 activity it is meant that the activity of CLC-2 is decreased by 10% or more, such as 20% or more, 30% or more, 40% or more, 50% or more, 60% or more, 70% or more, 80% or more, 90% or more, 95% or more (e.g., relative to a control in any convenient in vitro inhibition assay). In some cases modulating CLC-2 activity means decreasing the activity of the protein by a factor of 2 or more, such as 3 or more, 5 or more, 10 or more, 100 or more, or 1000 or more, relative to its normal activity (e.g., relative to a control as measured by any convenient assay).

In some cases, the method is a method of modulating CLC-2 activity in a sample. The term "sample" as used herein relates to a material or mixture of materials, typically, although not necessarily, in fluid form, containing one or more components of interest.

In some embodiments, there is provided a method of modulating CLC-2 activity, the method comprising contacting a sample with a subject compound (e.g., as described herein) to modulate the activity of CLC-2. In some cases, the sample is a cellular sample. The subject methods can provide for decreased activity of the CLC-2 chloride channel. By "decreasing activity of the CLC-2 chloride channel" is meant a level of activity in a cellular sample contacted with a subject compound, where the activity level in the sample is decreased by 10% or more, such as 20% or more, 30% or more, 40% or more, 50% or more, 60% or more, 70% or more, 80% or more, 90% or more, 100% or more, or even more, relative to a control sample that is not contacted with the subject compound.

In certain embodiments, the method of modulating CLC-2 activity is carried out with a compound as defined herein. In some embodiments, the CLC-2 modulating compound is a compound according to any one of formulas I, II or III. In some cases, the CLC-2 modulating compound is any one of the compounds depicted in FIG. 6.

In some embodiments, the subject compounds have an CLC-2 inhibition profile that reflects activity against additional proteins. In some embodiments, the subject compounds specifically inhibit CLC-2 without undesired inhibition of one or more other proteins.

In some embodiments, the subject compounds inhibit CLC-2, as determined by an inhibition assay, e.g., by an assay that determines the level of activity of the protein either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 μM or less, such as 3 μM or less, 1 μM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

As summarized above, aspects of the disclosure include methods of inhibiting CLC-2. A subject compound (e.g., as described herein) may inhibit at activity of CLC-2 in the range of 10% to 100%, e.g., by 10% or more, 20% or more, 30% or more, 40% or more, 50% or more, 60% or more, 70% or more, 80% or more, or 90% or more. In certain assays, a subject compound may inhibit its target with an $IC_{50}$ of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

The protocols that may be employed in determining CLC-2 activity are numerous, and include but are not limited to cell-free assays, e.g., binding assays; assays using purified enzymes, cellular assays in which a cellular phenotype is measured, e.g., gene expression assays; and in vivo assays that involve a particular animal (which, in certain embodiments may be an animal model for a condition related to the target pathogen).

In some embodiments, the subject method is an in vitro method that includes contacting a sample with a subject compound that specifically inhibits CLC-2. In certain embodiments, the sample is suspected of containing CLC-2 and the subject method further comprises evaluating whether the compound inhibits CLC-2.

In certain embodiments, the subject compound is a modified compound that includes a label, e.g., an affinity tag, an isotopic tag, or a fluorescent label, and the subject method further includes detecting the label, if present, in the sample, e.g., using optical detection or positron emission tomography (PET) imaging.

In certain embodiments, the compound is modified with a support or with affinity groups that bind to a support (e.g. biotin), such that any sample that does not bind to the compound may be removed (e.g., by washing). The specifically bound CLC-2, if present, may then be detected using any convenient means, such as, using the binding of a labeled target specific probe, or using a fluorescent protein reactive reagent.

In another embodiment of the subject method, the sample is known to contain CLC-2.

In some embodiments, the method is a method of reducing a disorder associated with CLC-2 malfunction, where the method includes contacting the cell with an effective amount of a subject compound (e.g., as described herein) to reduce proliferation of the disorder. In certain cases, the disorder associated with CLC-2 malfunction is a disorder affecting the Central Nervous System (CNS), diseases of the eye, post-operative scarring after glaucoma surgery, reproductive system disorders, and kidney disorders (e.g., as described herein).

Methods of Treatment

Aspects of the present disclosure include methods for modulating CLC-2 chloride channel activity in a subject suffering from a disease related to CLC-2 malfunction, comprising administering to the subject an effective amount of a subject compound (e.g. a meclofenamate derivative as described herein). In certain embodiments, the disease is selected from a disorder affecting the Central Nervous System (CNS), diseases of the eye, post-operative scarring after glaucoma surgery, reproductive system disorders, and kidney disorders.

The inventors have discovered that the subject compounds (e.g., as described herein) can have significant impact on modulating CLC-2 chloride channel activity. The results described and demonstrated herein indicate that CLC-2 inhibition according to the subject methods can modulate CLC-2 activity selectively, and thus find use in the treatment of a variety of diseases, e.g., as a target for diseases associated with CLC-2 malfunction (e.g., as described herein). As such, the subject methods can provide for inhibition of CLC-2 activity. In some instances, the subject method is a method for decreasing CLC-2 chloride channel activity in a subject. In some instances, the subject method is a method for modulating an immune response in a subject.

Aspects of the methods include administering to a subject with a disorder associated with CLC-2 malfunction a therapeutically effective amount of subject compound to treat the subject for the disorder. In some instances, the subject is one who is diagnosed with or suspected of having a disorder associated with CLC-2 malfunction. Any convenient subject compound can be used in the subject methods of treating the disorder associated with CLC-2 malfunction. In certain cases, the compound is a compound as described herein. In some cases, the disorder is a disease of the central nervous system (CNS). In some cases, the disease is selected from epilepsy, leukoencephalopathy (white-matter degeneration), and gliomas. In certain cases, the disease is of the eye. In certain cases, the disease of the eye is retinal degeneration. In certain cases, the disorder is post-operative scarring after glaucoma surgery. In certain cases, the disease is a reproductive system disorder. In certain cases, the reproductive system disorder is testes degeneration, or azoospermia. In certain cases, the disease is a kidney disorder. In certain cases, the kidney disorder is primary aldosteronism or hypertension.

In some embodiments of the methods disclosed herein, the compound is described by any one of formulas I, II or III. In some cases, the compound is any one of compounds depicted in FIG. 6.

In certain embodiments of the methods disclosed herein, the compound is selected from:

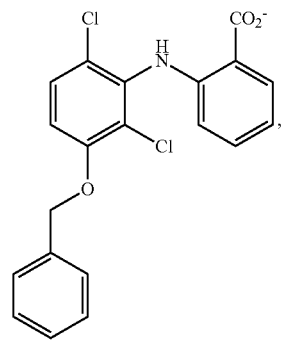
AK3-99B

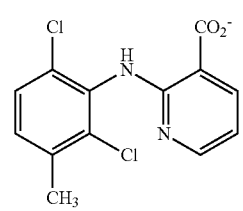
AK3-108B

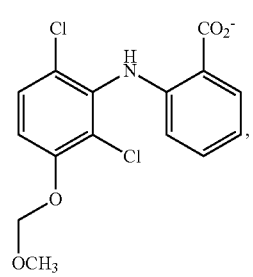
AK3-99A

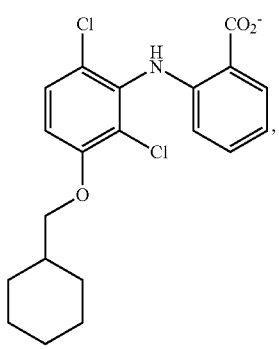
AK3-101A

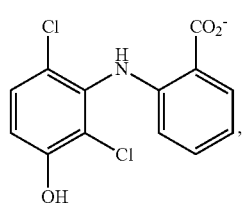
AK3-102A

-continued
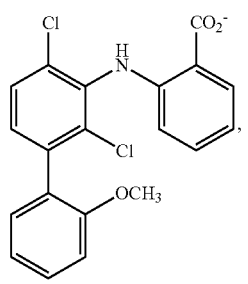  AK3-101B
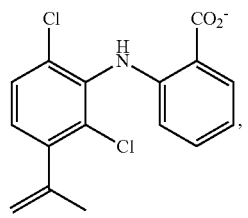  AK2-289B
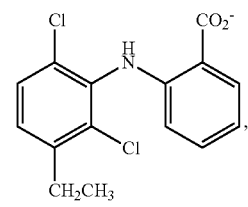  AK2-292
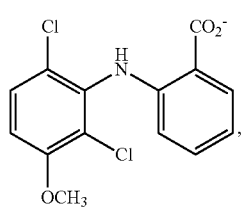  AK3-289A
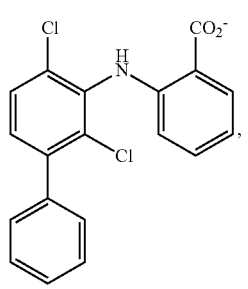  AK3-100A
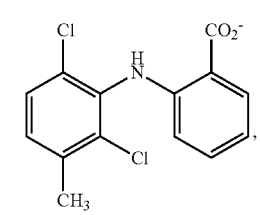  MCFA
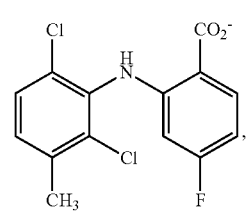  AK3-98A
-continued
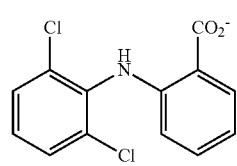  AK2-209A
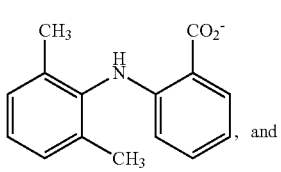  AK2-289C
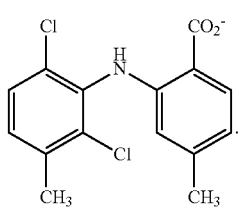  AK2-288A
In certain embodiments of the methods disclosed herein, the compound is selected from:
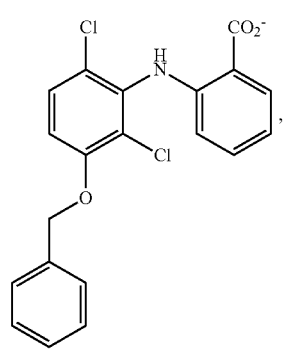  AK3-99B
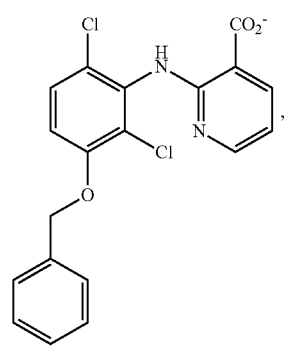  AK3-238

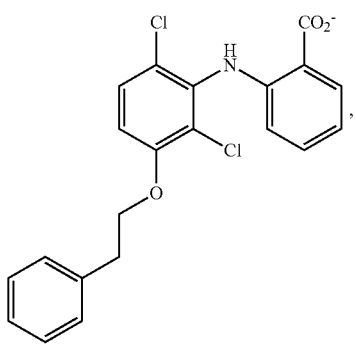
EEGI-060
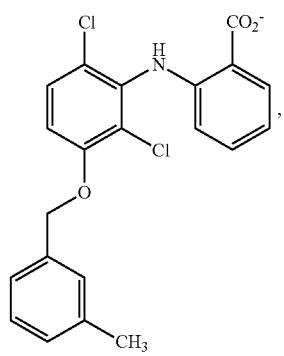
EEGI-054
AK3-261
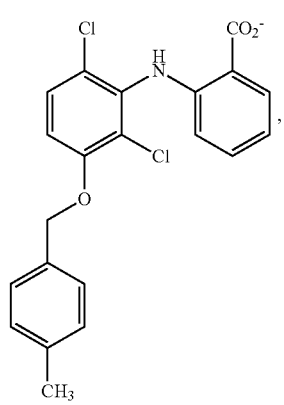
EEGI-056
EEFI-059
AK3-225
EEGI-055
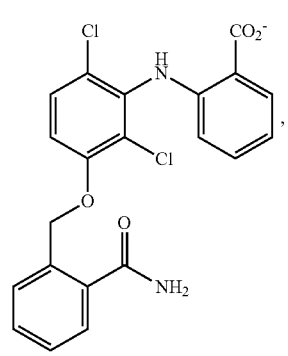
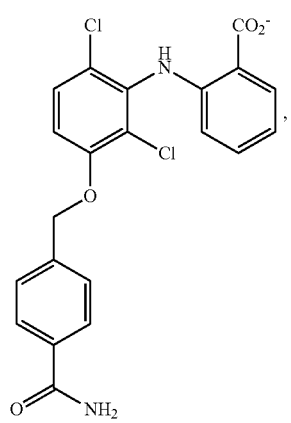
AK3-219

AK3-250

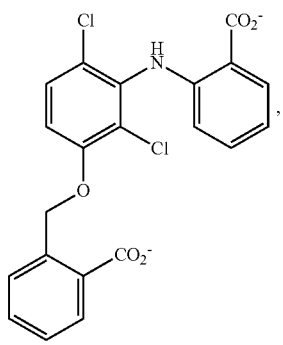

AK3-239

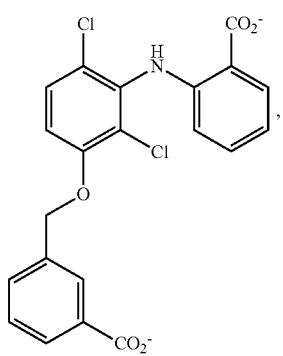

AK3-224

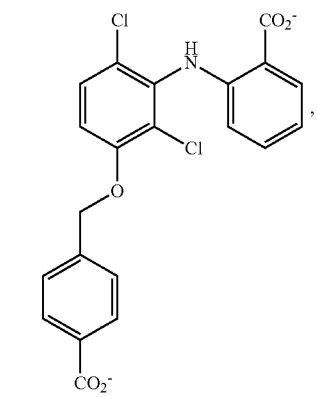

AK3-226

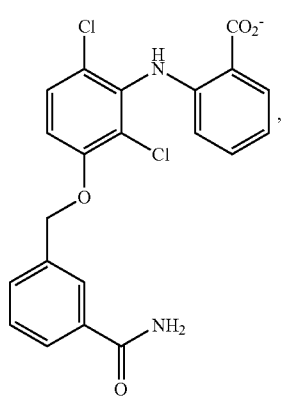

AK3-227

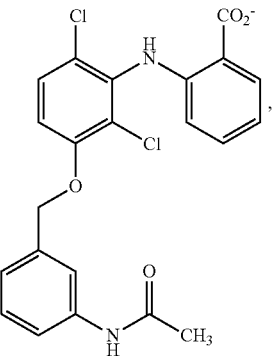

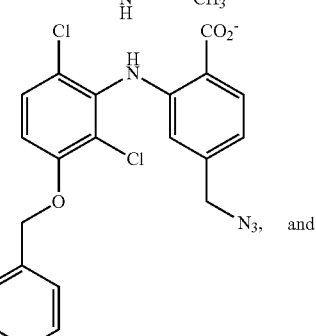

and

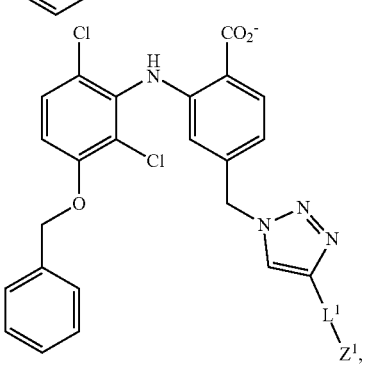

wherein:
$L^1$ is a PEG linker,
$Z^1$ is a biotin moiety.

In certain embodiments of the subject methods, the compound is AK3-238 (also referred to herein as FA44).

In certain embodiments of the subject methods, the compound is AK3-99B (also referred to herein as FA26). As such, aspects of the method include contacting a sample with a subject compound (e.g., as described above) under conditions by which the compound inhibits CLC-2. Any convenient protocol for contacting the compound with the sample may be employed. The particular protocol that is employed may vary, e.g., depending on whether the sample is in vitro or in vivo. For in vitro protocols, contact of the sample with the compound may be achieved using any convenient protocol. In some instances, the sample includes cells that are maintained in a suitable culture medium, and the complex is introduced into the culture medium. For in vivo protocols, any convenient administration protocol may be employed. Depending upon the potency of the compound, the cells of interest, the manner of administration, the number of cells present, various protocols may be employed.

In some embodiments, the subject method is a method of treating a subject for a disorder associated with CLC-2 malfunction (e.g., as described herein). In some embodiments, the subject method includes administering to the subject an effective amount of a subject compound (e.g., as described herein) or a pharmaceutically acceptable salt thereof. The subject compound may be administered as part of a pharmaceutical composition (e.g., as described herein). In certain instances of the method, the compound that is administered is a compound of one of formulae (I), (II), or (III). In certain instances of the method, the compound that is administered is described by one of the compounds of FIG. 6. In certain instances of the method, the compound that is administered is AK3-99B (also referred to herein as FA26). In certain instances of the method, the compound that is administered is AK3-238 (also referred to herein as FA44).

In some embodiments, an "effective amount" is an amount of a subject compound that, when administered to an individual in one or more doses, in monotherapy or in combination therapy, is effective to inhibit CLC-2 by about 20% (20% inhibition), at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), compared to the CLC-2 activity in the individual in the absence of treatment with the compound, or alternatively, compared to the CLC-2 activity in the individual before or after treatment with the compound.

In some embodiments, an effective amount of a compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of a compound is administered. In other embodiments, multiple doses are administered. Where multiple doses are administered over a period of time, the compound can be administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Administration of a therapeutically effective amount of a subject compound to an individual with a disorder associated with CLC-2 malfunction can result in one or more of: 1) a reduction in CLC-2 activity; 2) a reduction in the spread of the disorder from one cell to another cell in an individual; 4) a reduction of morbidity or mortality in clinical outcomes; 5) shortening the total length of treatment when combined with other active agents; and 6) an improvement in an indicator of disease response (e.g., a reduction in one or more symptoms of the disorder). Any of a variety of methods can be used to determine whether a treatment method is effective. For example, a biological sample obtained from an individual who has been treated with a subject method can be assayed.

In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). The subject may be in need of treatment for a disorder associated with CLC-2 malfunction. In some instances, the subject methods include diagnosing a condition associated with CLC-2 malfunction, including any one of the specific disorders described herein. In some embodiments, the compound is administered as a pharmaceutical preparation. In certain embodiments of the methods, the compound is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p 977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is unlabeled and a secondary labeling agent is used for imaging.

Kits

Aspects of the invention further include kits for use in practicing the subject methods and compositions. The compounds of the invention can be included as reagents in kits for use in, for example, the methodologies described above.

A kit can include a compound (e.g., as described herein); and one or more components selected from the group consisting of an additional active agent, a buffer, a solvent, a standard and instructions for use.

The one or more components of the kit may be provided in separate containers (e.g., separate tubes, bottles, or wells in a multi-well strip or plate).

The compounds of the kits may be provided in a liquid composition, such as any suitable buffer. Alternatively, the compounds of the kits may be provided in a dry composition (e.g., may be lyophilized), and the kit may optionally include one or more buffers for reconstituting the dry compound. In certain aspects, the kit may include aliquots of the compound provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The compounds and methods of the invention, e.g., as described herein, find use in a variety of applications. Applications of interest include, but are not limited to: research applications and therapeutic applications. Methods of the invention find use in a variety of different applications including any convenient application where treatment of a disorder associated with CLC-2 malfunction, e.g., a disorder of the CNS etc., is desired.

The subject compounds and methods find use in a variety of research applications. The subject compounds and methods may be used in the optimization of the bioavailability and metabolic stability of compounds. The subject compounds and methods may find us as diagnostic tools, e.g., in diagnosing a cancer.

The subject compounds and methods find use in a variety of therapeutic applications. Therapeutic applications of interest include those applications in which CLC-2 malfunction is the cause or a compounding factor in disease progression. As such, the subject compounds find use in the treatment of a variety of different conditions in which the modulation of CLC chloride channel is desired. For example, the subject compounds and methods may find use in treating a disease associated with CLC-2 malfunction (e.g., as described herein), such as a disorder of the CNS, eye disease, reproductive disorder or a kidney disorder.

As such, the subject compounds find use in the treatment of a variety of different conditions in which the modulation of CLC-2 chloride channel in the host is desired.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Compound Screen

To identify a lead compound against CLC-2, we have worked with ChanTest Corporation to develop a medium-throughput screen, employing IonWorks Barracuda automated patch-clamp instrumentation and a human CLC-2 cell line. Using the validated assay, a focused compound library consisting of 800 FDA-approved compounds and natural products was screened at 30 µM (FIG. 1). Twenty-seven compounds were found to inhibit >20% of the CLC-2 current, and five of these inhibited >50%. The top scoring compound was a nonsteroidal anti-inflammatory drug (NSAID), meclofenamate ($IC_{50}$=14 µM), which we targeted for further development. Although still in the low-µM range, the potency of this compound is a significant improvement over that of all previously reported small-molecule inhibitors of CLC-2 (NPPB, DIDS, 9-AC, DPC), which all have potencies in the mM range.

Example 2: Compound Synthesis

Figure 2:
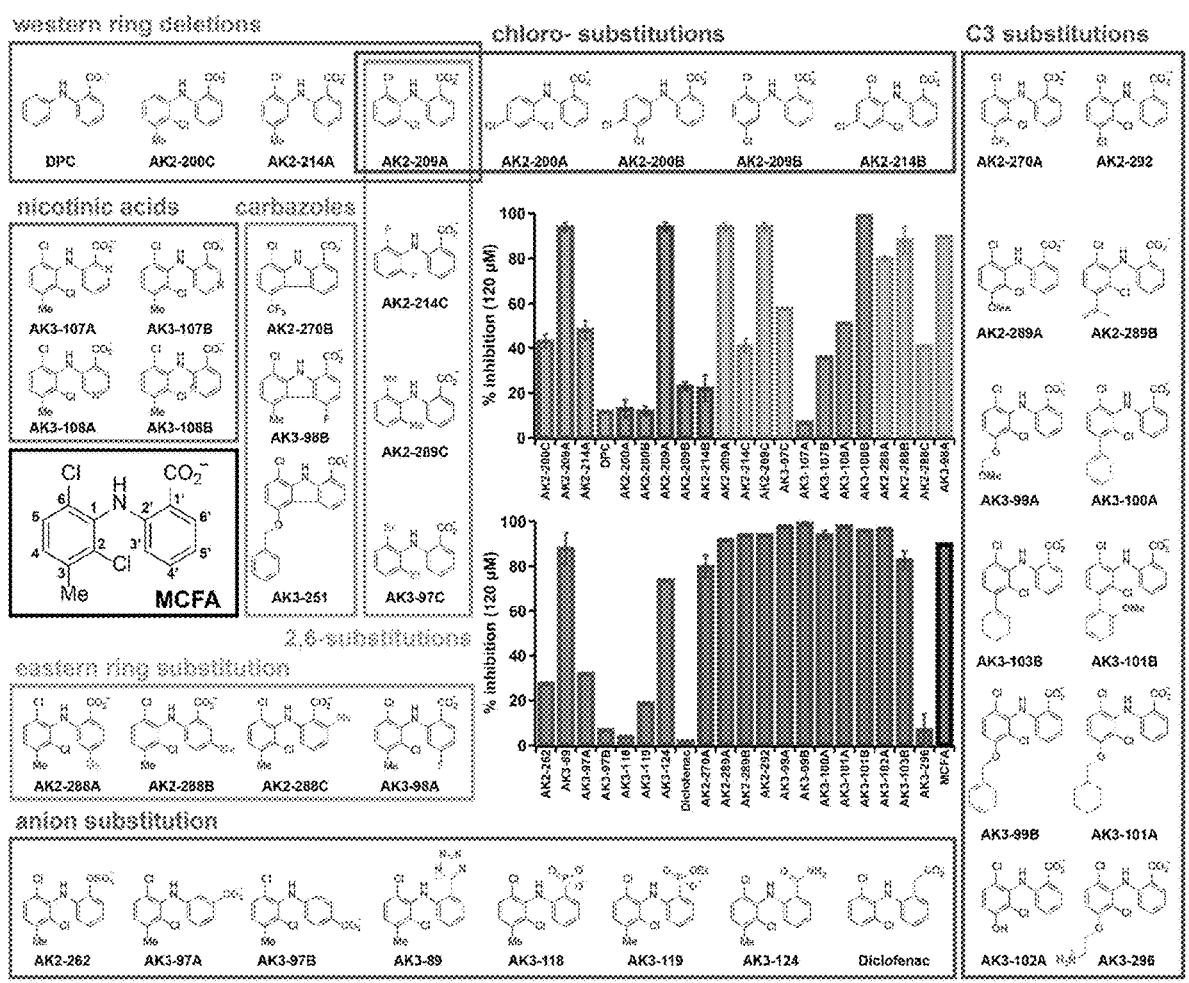
FIG. 2 illustrates structure-activity relationship (SAR) studies of meclofenamate (MCFA) derivatives against CLC-2. Bar graph depicts % inhibition of CLC-2 current at −120 mV with 120 µM of each compound.

To date, we have performed three rounds of structure-activity relationship (SAR) studies in which we prepared and tested a total of 56 meclofenamate (MCFA) derivatives against CLC-2 (FIG. 2). These compounds are accessible through a short, 2-5 step synthetic route that ends with a Buchwald-Hartwig coupling of an aniline and aryl bromide with subsequent ester hydrolysis (Scheme 1).

Scheme 1. General synthesis route developed for MCFA derivatives.

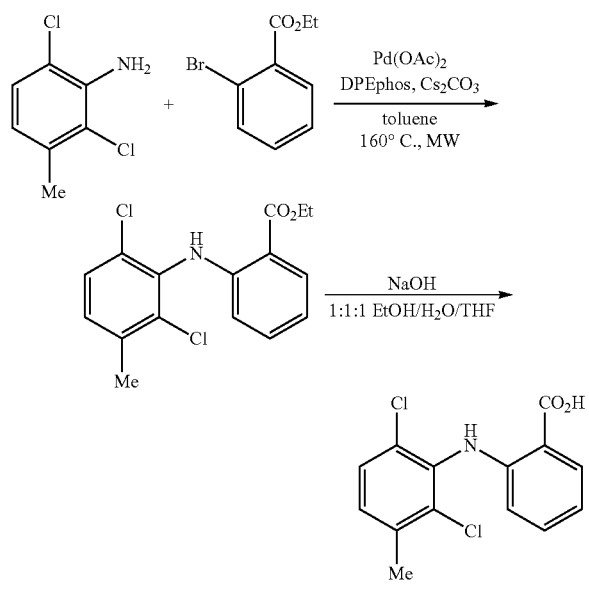

More generally, the subject compounds may be prepared using any convenient method. Many general references providing commonly known chemical synthetic schemes and conditions useful for synthesizing the disclosed compounds are also available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). Reactions may be monitored by thin layer chromatography (TLC), LC/MS and reaction products characterized by LC/MS and $^1$H NMR. Intermediates and final products may be purified by silica gel chromatography or by reverse phase HPLC.

Example 3: Compound Activity Against CLC-2

Figure 3:
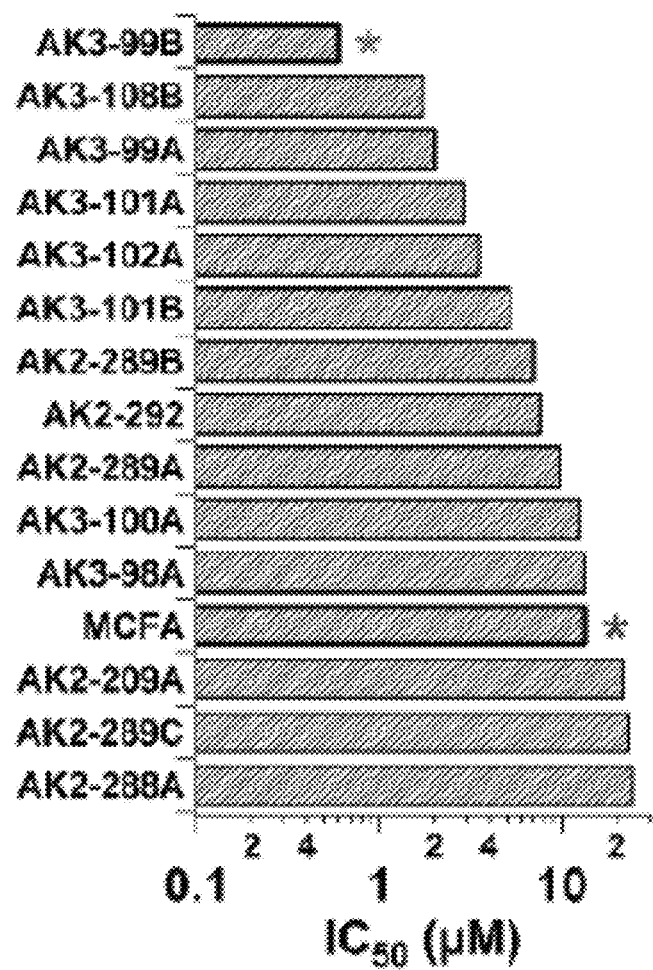
FIG. 3 shows fifteen of the meclofenamate derivatives screened against CLC-2 with $IC_{50}$ values in logarithmic scale. AK3-99B is the most effective compound from this series with an $IC_{50}$ of ~600 nM, and MCFA is the original lead compound (AK3-099B and MCFA are each indicated with an asterisk).

Based on results from our first two rounds of SAR, compounds designed in round three included a variety of substituents at the C3 position on the western ring. Such substitutions yielded our most potent compounds, for example, the OBn-substituted compound, AK3-99B ($IC_{50}$=600 nM, Table 1, FIG. 3) and AK3-238 (IC50=17±2 nM, Table 1 and FIG. 7). Note, compound AK3-99B is also referred to herein as FA26; and compound AK3-238 is also referred to herein as FA44. Compound AK3-238 has approximately 10,000 times greater potency towards CLC-2 compared to the most closed related CLC homolog, CLC-1. In just three rounds of SAR with only 56 compounds, we have improved potency by over 20-fold and developed the most potent small-molecule CLC-2 inhibitors known. Studies are underway to continue improving potency of these molecules, as well as evaluate selectivity and specificity in the context of the CNS.

Figure 7:
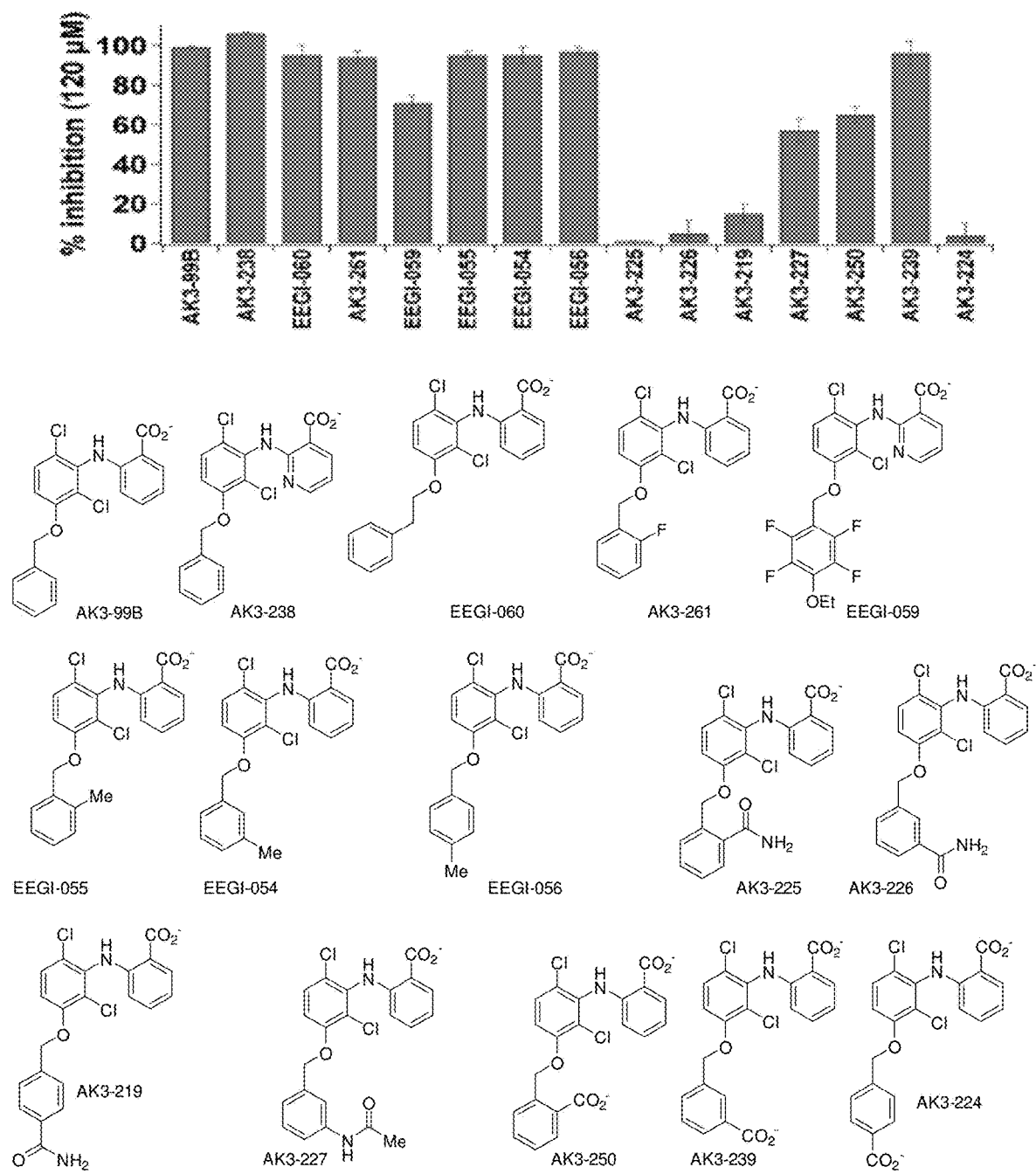
FIG. 7 shows derivatives of AK3-99B, including AK3-238 which showed an even higher efficacy than AK3-99B, as explained and illustrated in Table 1.

Table 1 shows $IC_{50}$ values of fenamate derivative compounds. AK3-238 showed the highest potency with an $IC_{50}$ value of below 0.12 μM, as explained and illustrated in Table 1. AK3-238 and other AK3-99B derivatives are shown in FIG. 7.

TABLE 1

$IC_{50}$ values of fenamate derivatives against CLC-2. Values were determined on n = 4 cells based on four concentrations (variable by compound) of each compound using the IonWorks ™ Barracuda automated patch clamp electrophysiology system. If the $IC_{50}$ was greater than the highest concentration tested, this concentration is listed along with the % inhibition at this concentration (in parentheses). If a compound elicited an increase in peak current instead of inhibition, values are report as a negative percentage, and the compound is marked with an asterisk.

| Compound | $IC_{50}$ (μM) |
|---|---|
| AK2-200A | >120 (13%) |
| AK2-200B | >120 (12%) |
| AK2-200C | >120 (43%) |
| AK2-209A | 22.10 |
| AK2-209B | >120 (23%) |
| AK2-214A | >120 (48%) |
| AK2-214B | >120 (22%) |
| AK2-214C | >120 (41%) |
| AK2-262 | >120 (28%) |
| AK2-270A | 35.66 |
| AK2-270B* | >120 (−48%) |
| AK2-288A | 24.66 |
| AK2-288B | 37.86 |
| AK2-288C | >102 (37%) |
| AK2-289A | 9.86 |
| AK2-289B | 7.16 |
| AK2-289C | 23.45 |
| AK2-292 | 7.69 |
| AK3-89 | 33.37 |
| AK3-97A | >141 (36%) |
| AK3-97B | >144 (8%) |
| AK3-97C | 86.32 |
| AK3-98A | 13.67 |
| AK3-98B* | >69 (−16%) |
| AK3-99A | 2.04 |
| AK3-99B | 0.62 |
| AK3-100A | 12.60 |
| AK3-101A | 2.98 |
| AK3-101B | 5.29 |
| AK3-102A | 3.60 |
| AK3-103B | 48.83 |
| AK3-107A | >222 (12%) |
| AK3-107B | >42 (16%) |
| AK3-108A | 115.17 |
| AK3-108B | 1.79 |
| AK3-118 | >195 (6%) |
| AK3-119 | >354 (41%) |
| AK3-124 | 42.36 |
| AK3-219 | >120 (15%) |
| AK3-224 | >120 (4%) |
| AK3-225 | >120 (0%) |
| AK3-226 | >120 (5%) |
| AK3-227 | 81.91 |
| AK3-238 | <0.12 (90%) |
| AK3-239 | 17.91 |
| AK3-250 | 67.80 |
| AK3-251 | >120 (5%) |
| AK3-261 | 1.16 |
| AK3-294 | 77.09 |
| AK3-296 | >120 (7%) |
| AK3-298 | >55 (28%) |
| DPC | >312 (27%) |
| Diclofenac | >363 (5%) |
| EEGI-054 | 7.93 |
| EEGI-055 | 1.20 |
| EEGI-056 | 15.82 |
| EEGI-059 | 76.15 |
| EEGI-060 | 7.32 |
| MCFA | 13.88 |
| NFA | >120 (0%) |

Example 4: Selectivity Data

Figure 4:
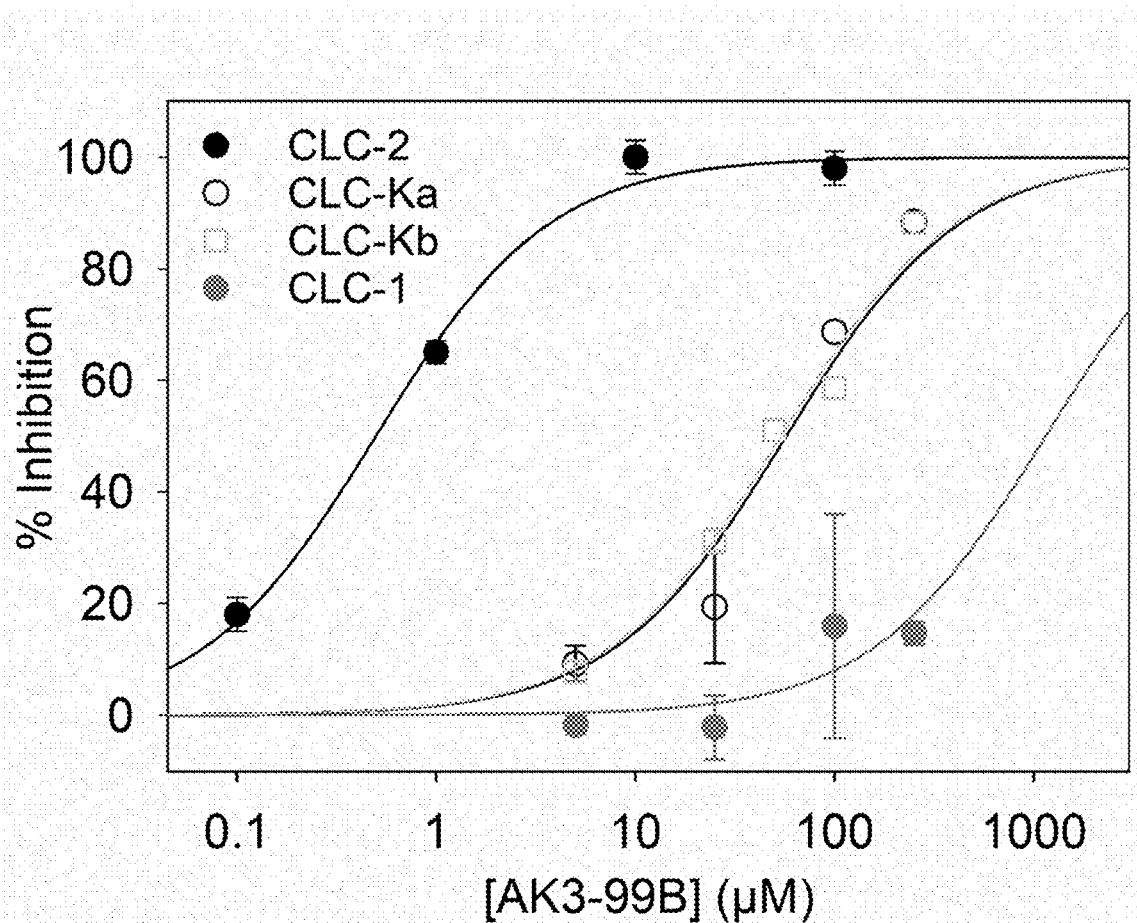
FIG. 4 shows preliminary data indicating that compound AK3-99B, is selective for CLC-2 among the most closely related CLC homologs, CLC-Ka, CLC-Kb, and CLC-1.

Preliminary data acquired in our lab by two-electrode voltage clamp electrophysiology in *Xenopus* oocytes indicate that compound AK3-99B is selective for CLC-2 among the four most closely related CLC homologs CLC-1, CLC-2, CLC-Ka, and CLC-Kb. The $IC_{50}$ against CLC-Ka and CLC-Kb is between 50 and 100 µM, and the $IC_{50}$ against CLC-1 is >250 µM (FIG. 4).

Our exemplary molecule, FA44, has an $IC_{50}$ of 17±2 nM against CLC-2 and 10,000 times greater potency towards CLC-2 compared to the most closely related CLC homolog, CLC-1. In addition to extraordinary selectivity within the CLC family, we have demonstrated that this molecule is highly specific for CLC-2 within the context of the brain, showing no off-target effects among a diverse panel of CNS receptors, channels, and transporters that we screened.

Table 2 shows the $IC_{50}$ values for exemplary compounds, FA26 (AK3-99B), FA35 (AK3-108B) and FA44 (AK3-238), against CLC-1 and CLC-2. If the $IC_{50}$ was greater than the highest concentration tested, this concentration is listed along with the percent inhibition at this concentration (in parenthesis).

TABLE 2

$IC_{50}$ values for exemplary compounds against CLC-1 and CLC-2

| Compound | $IC_{50}$ (CLC-2) | $IC_{50}$ (CLC-1) |
|---|---|---|
| MCFA | 8.7 ± 0.3 µM | 60 ± 9 µM |
| FA26 | 1.7 ± 0.2 µM | >30 µM (25%) |
| FA35 | 4.0 ± 0.7 µM | >30 µM (5%) |
| FA44 | 17 ± 2 nM | >100 µM (22%) |

Figure 8:
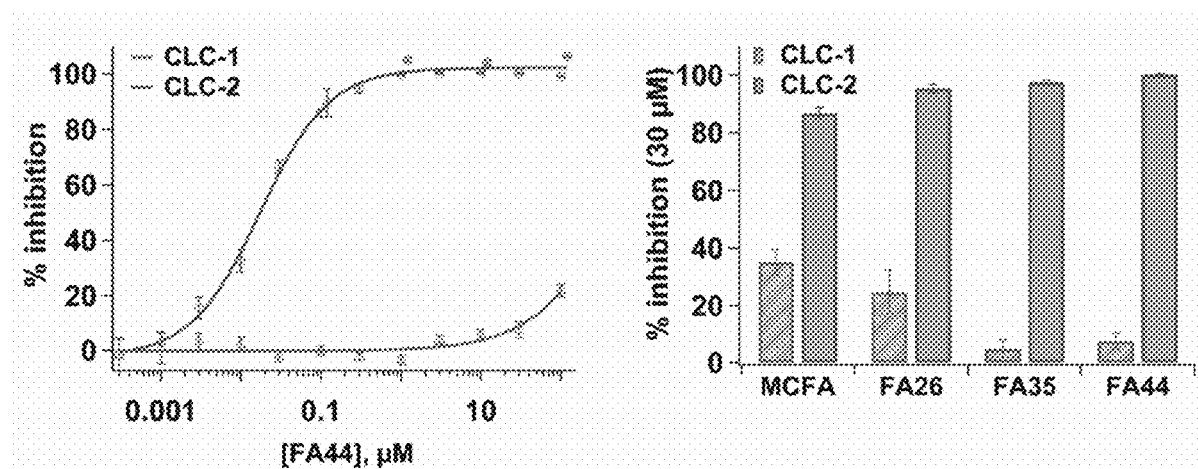
FIG. 8, panel A illustrates that compound FA44 (also referred to herein as AK3-238) is selective for CLC-2 over CLC-1, the most closely related CLC homolog.

FIG. 8, panels A and B depict graphically the Selectivity between CLC-1 and CLC-2. Panel A shows the inhibition curve for FA44 against human CLC-2 (high curve) compared to human CLC-1 (low curve), the most closely related CLC homolog. Data points represent the mean current block at 16 different FA44 concentrations (n=4-8), using the IonWorks™ Barracuda. The $IC_{50}$ for FA44 based on this data is 17±2 nM. Results shown are data at −120 mV; however, inhibition is not significantly voltage dependent. Panel B depicts a summary graph showing the mean inhibition of CLC-1 (left bar) or CLC-2 (right bar) current at 30 µM, illustrating the improvement in both selectivity and potency from the hit compound MCFA to the exemplary compound FA44.

New CNS Specificity Data for AK3-238 (FA44) and AK3-99B (FA26)

Two exemplary compounds, FA44 and FA26, were screened against a panel of CNS receptors, transporters, and ion channels to examine specificity for CLC-2 in the brain. A comprehensive primary binding assay screen was performed through the NIH Psychoactive Drug Screening Program (PDSP) at UNC-Chapel Hill. Secondary or functional assays were performed for compounds showing >50% activity in the primary assay. All results are shown in the Table 3 below.

TABLE 3

Primary binding assay data for FA26 and FA44. $K_i$ values are only reported for compounds eliciting >50% activity in a primary binding assay at 10 µM. Entries marked with * denote that only a functional assay was performed.

| | | FA26 | | FA44 | |
|---|---|---|---|---|---|
| Entry | Receptor | % (10 µM) | $K_i$ | % (10 µM) | $K_i$ |
| 1 | 5-HT1A | 50.00 | >10 µM | 53.99 | >10 µM |
| 2 | 5-HT1B | −0.25 | — | 49.89 | — |
| 3 | 5-HT1D | 6.77 | — | 44.06 | — |
| 4 | 5-HT1E | 11.82 | — | 10.43 | — |
| 5 | 5-HT2A | 19.70 | — | 18.91 | — |
| 6 | 5-HT2B | 14.38 | — | 45.16 | — |
| 7 | 5-HT2C | −11.17 | — | −13.39 | — |
| 8 | 5-HT3 | −7.63 | — | 28.75 | — |
| 9 | 5-HT5A | −5.77 | — | 28.19 | — |
| 10 | 5-HT6 | −10.67 | — | 18.68 | — |
| 11 | 5-HT7 | −29.75 | — | 17.51 | — |
| 12 | A2A | — | — | −8.70 | — |
| 13 | Alpha1A | 24.26 | — | 12.29 | — |
| 14 | Alpha1B | 4.33 | — | 4.90 | — |
| 15 | Alpha1D | 7.20 | — | −10.12 | — |
| 16 | Alpha2A | 65.08 | 3 µM | −2.55 | — |
| 17 | Alpha2B | 15.62 | — | −28.62 | — |
| 18 | Alpha2C | 17.28 | — | 3.41 | — |
| 19 | AMPA | 21.14 | — | 28.20 | — |
| 20 | Beta1 | −13.11 | — | 22.04 | — |
| 21 | Beta2 | −8.08 | — | 4.77 | — |
| 22 | Beta3 | 32.58 | — | 24.76 | — |
| 23 | BZP rat brain site | 40.75 | — | 29.32 | — |
| 24 | Calcium channel | 12.22 | — | 23.69 | — |
| 25 | D1 | 27.05 | — | −9.96 | — |
| 26 | D2 | −6.96 | — | 7.69 | — |
| 27 | D3 | 18.42 | — | −4.66 | — |
| 28 | D4 | −0.19 | — | −0.65 | — |
| 29 | D5 | 27.29 | — | 31.58 | — |
| 30 | DAT | −17.73 | — | 9.23 | — |
| 31 | DOR | 16.22 | — | 16.59 | — |
| 32 | $GABA_A$ | −17.65 | — | −4.29 | — |
| 33 | H1 | −4.62 | — | 15.48 | — |
| 34 | H2 | 25.62 | — | 5.35 | — |
| 35 | H3 | −5.97 | — | −0.92 | — |
| 36 | H4 | 8.29 | — | 2.23 | — |
| 37 | HERG | −15.95 | — | −43.87 | >10 µM |
| 38 | KA | 13.56 | — | 36.60 | — |
| 39 | KOR | 29.90 | — | 4.11 | — |
| 40 | M1 | 58.54 | >10 µM | 11.29 | — |
| 41 | M2 | 14.57 | — | −8.25 | — |
| 42 | M3 | 65.66 | >10 µM | 54.64 | >3 µM |
| 43 | M4 | −3.01 | — | 56.16 | >5 µM |
| 44 | M5 | 56.99 | >10 µM | 13.55 | >10 µM |
| 45 | mGluR1* | — | >10 µM | — | >10 µM |
| 46 | mGluR2* | — | >10 µM | — | — |
| 47 | mGluR4* | — | >10 µM | — | — |
| 48 | mGluR5 | 47.44 | >10 µM | 57.39 | >10 µM |
| 49 | mGluR6* | — | >10 µM | — | — |
| 50 | mGluR8* | — | >10 µM | — | — |
| 51 | MOR | 9.03 | — | −0.18 | — |
| 52 | NET | 33.59 | — | 17.36 | — |
| 53 | NMDA | 39.29 | — | 24.18 | — |
| 54 | NOP | 24.65 | — | 21.14 | — |
| 55 | Oxytocin | 8.80 | — | −1.41 | — |
| 56 | PBR | 2.28 | — | 8.22 | — |
| 57 | SERT | 4.65 | — | 30.25 | — |
| 58 | Sigma 1 | 3.95 | — | 38.52 | — |
| 59 | Sigma 2 | −9.10 | — | −8.14 | — |
| 60 | Smoothened | — | — | — | — |
| 61 | V1A | — | — | 23.96 | — |
| 62 | V1B | — | — | 40.53 | — |
| 63 | Y2 | — | — | — | — |

The discovery of FA44 represents an unprecedented breakthrough in CLC channel pharmacology and will enable systematic investigations into CLC biophysics and physiology that have never before been possible. Such tools should enable study of CLC-2 in the CNS and its potential role in white matter degeneration and epilepsy. Understanding the physiological role of CLC-2 in neurons and glia will permit the development of targeted therapies for diseases of the CNS and other diseases related to CLC-2 malfunction (e.g., as described herein).

Figure 5:
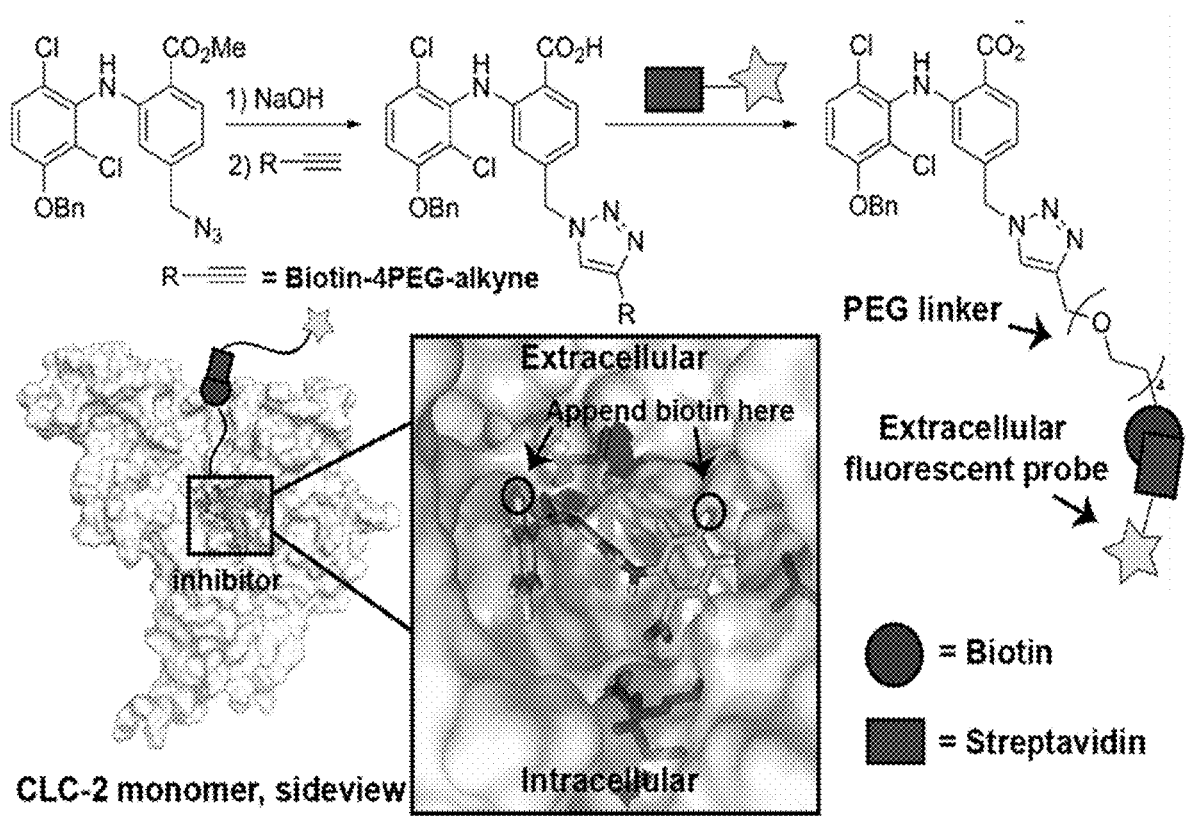
FIG. 5 illustrates a strategy for CLC-2 imaging using MCFA-based probes.

Another current direction is the development of small-molecule probes for imaging or channel pull-down. This can be achieved by a variation on our current SAR synthetic strategy. Installation of an azide or alkyne onto the MCFA scaffold will allow us to perform azide-alkyne click chemistry to append biotin from commercially available biotin-azides or alkynes that contain PEG linkers of various lengths (see, e.g., FIG. 5). We can employ fluorescently-labeled streptavidin with these types of MCFA-derived probes to image CLC-2 in neurons. This will represent a major advance, as currently available antibodies fail this test. Docking of AK3-99B to our computational models of CLC-2 suggests that the hydrophobic pockets housing the —OBn group extend upward toward the extracellular side of the protein, perhaps providing ideal points of attachment for molecular probe linkers (FIG. 5).

Introducing a $^{18}F$ or $^{11}C$ label into the subject compounds can allow for the compounds to be used in positron emission tomography (PET) imaging. CLC-2 overexpression has been associated with glioblastoma, according attaching an isotopic label such as $^{18}F$, can allow for use of a subject compound as a cancer diagnostic.

There are currently no tools available of this kind to be able to isolate, image, and study CLC-2 in the brain. Potent small-molecule tools are needed to elucidate the role of CLC-2 in the CNS, both in neurological disorders and in normal, healthy brain tissue. Exemplary compound AK3-238 represents a promising molecule for this purpose.

REFERENCES (1) Stauber, T.; Weinert, S.; Jentsch, T. J. Cell Biology and Physiology of CLC Chloride Channels and Transporters. In *Comprehensive Physiology*; John Wiley & Sons, Inc., 2012.

(2) Stölting, G.; Fischer, M.; Fahlke, C. CLC Channel Function and Dysfunction in Health and Disease. *Front. Physiol.* 2014, 5.

(3) Jin, Y.; Blikslager, A. T. ClC-2 Regulation of Intestinal Barrier Function: Translation of Basic Science to Therapeutic Target. *Tissue Barriers* 2015, 3 (4), e1105906.

(4) Bi, M. M.; Hong, S.; Zhou, H. Y.; Wang, H. W.; Wang, L. N.; Zheng, Y. J. Chloride Channelopathies of ClC-2. *Int. J. Mol. Sci.* 2013, 15 (1), 218-249.

(5) Kramer, B. K.; Bergler, T.; Stoelcker, B.; Waldegger, S. Mechanisms of Disease: The Kidney-Specific Chloride Channels ClCKA and ClCKB, the Barttin Subunit, and Their Clinical Relevance. *Nat. Clin. Pract. NephroL* 2008, 4(1), 38-46.

(6) Jeworutzki, E.; López-Hernandez, T.; Capdevila-Nortes, X.; Sirisi, S.; Bengtsson, L.; Montolio, M.; Zifarelli, G.; Arnedo, T.; Müller, C. S.; Schulte, U.; Nunes, V.; Martinez, A.; Jentsch, T. J.; Gasull, X.; Pusch, M.; Estévez, R. GlialCAM, a Protein Defective in a Leukodystrophy, Serves as a ClC-2 Cl– Channel Auxiliary Subunit. *Neuron* 2012, 73 (5), 951-961.

(7) Thiemann, A.; Grunder, S.; Pusch, M.; Jentsch, T. J. A Chloride Channel Widely Expressed in Epithelial and Non-Epithelial Cells. *Nature* 1992, 356 (6364), 57-60.

(8) Haug, K.; Warnstedt, M.; Alekov, A. K.; Sander, T.; Ramírez, A.; Poser, B.; Maljevic, S.; Hebeisen, S.; Kubisch, C.; Rebstock, J.; Horvath, S.; Hallmann, K.; Dullinger, J. S.; Rau, B.; Haverkamp, F.; Beyenburg, S.; Schulz, H.; Janz, D.; Giese, B.; Müller-Newen, G.; Propping, P.; Elger, C. E.; Fahlke, C.; Lerche, H.; Heils, A. Mutations in CLCN2 Encoding a Voltage-Gated Chloride Channel Are Associated with Idiopathic Generalized Epilepsies. *Nat. Genet.* 2003, 33 (4), 527-532.

(9) Saint-Martin, C.; Gauvain, G.; Teodorescu, G.; Gourfinkel-An, I.; Fedirko, E.; Weber, Y. G.; Maljevic, S.; Ernst, J.-P.; Garcia-Olivares, J.; Fahlke, C.; Nabbout, R.; LeGuern, E.; Lerche, H.; Poncer, J. C.; Depienne, C. Two Novel CLCN2 Mutations Accelerating Chloride Channel Deactivation Are Associated with Idiopathic Generalized Epilepsy. *Hum. Mutat.* 2009, 30 (3), 397-405.

(10) Kleefuß-Lie, A.; Friedl, W.; Cichon, S.; Haug, K.; Warnstedt, M.; Alekov, A.; Sander, T.; Ramirez, A.; Poser, B.; Maljevic, S.; Hebeisen, S.; Kubisch, C.; Rebstock, J.; Horvath, S.; Hallmann, K.; Dullinger, J. S.; Rau, B.; Haverkamp, F.; Beyenburg, S.; Schulz, H.; Janz, D.; Giese, B.; Müller-Newen, G.; Propping, P.; Elger, C. E.; Fahlke, C.; Lerche, H. CLCN2 Variants in Idiopathic Generalized Epilepsy. *Nat. Genet.* 2009, 41 (9), ng0909-954-954.

(11) D'Agostino, D.; Bertelli, M.; Gallo, S.; Cecchin, S.; Albiero, E.; Garofalo, P. G.; Gambardella, A.; Hilaire, J.-M. S.; Kwiecinski, H.; Andermann, E.; Pandolfo, M. Mutations and Polymorphisms of the CLCN2 Gene in Idiopathic Epilepsy. *Neurology* 2004, 63 (8), 1500-1502.

(12) Niemeyer, M. I.; Cid, L. P.; Sepulveda, F. V.; Blanz, J.; Auberson, M.; Jentsch, T. J. No Evidence for a Role of CLCN2 Variants in Idiopathic Generalized Epilepsy. *Nat. Genet.* 2010, 42 (1), ng0110-3-3.

(13) Blanz, J.; Schweizer, M.; Auberson, M.; Maier, H.; Muenscher, A.; Hübner, C. A.; Jentsch, T. J. Leukoencephalopathy upon Disruption of the Chloride Channel ClC-2. *J. Neurosci. Off. J. Soc. Neurosci.* 2007, 27(24), 6581-6589.

(14) Depienne, C.; Bugiani, M.; Dupuits, C.; Galanaud, D.; Touitou, V.; Postma, N.; van Berkel, C.; Polder, E.; Tollard, E.; Darios, F.; Brice, A.; de Die-Smulders, C. E.; Vles, J. S.; Vanderver, A.; Uziel, G.; Yalcinkaya, C.; Frints, S. G.; Kalscheuer, V. M.; Klooster, J.; Kamermans, M.; Abbink, T. E.; Wolf, N. I.; Sedel, F.; van der Knaap, M. S. Brain White Matter Oedema Due to ClC-2 Chloride Channel Deficiency: An Observational Analytical Study. *Lancet Neurol.* 2013, 12 (7), 659-668.

(15) Olsen, M. L.; Schade, S.; Lyons, S. A.; Amaral, M. D.; Sontheimer, H. Expression of Voltage-Gated Chloride Channels in Human Glioma Cells. *J. Neurosci.* 2003, 23 (13), 5572-5582.

(16) Ransom, C. B.; O'Neal, J. T.; Sontheimer, H. Volume-Activated Chloride Currents Contribute to the Resting Conductance and Invasive Migration of Human Glioma Cells. *J. Neurosci.* 2001, 21 (19), 7674-7683.

(17) Soroceanu, L.; Manning, T. J.; Sontheimer, H. Modulation of Glioma Cell Migration and Invasion Using Cl– and K+ Ion Channel Blockers. *J. Neurosci.* 1999, 19 (14), 5942-5954.

(18) Verkman, A. S.; Galietta, L. J. V. Chloride Channels as Drug Targets. *Nat. Rev. Drug Discov.* 2009, 8 (2), 153-171.

(19) Furukawa, T.; Ogura, T.; Katayama, Y.; Hiraoka, M. Characteristics of Rabbit ClC-2 Current Expressed in *Xenopus* Oocytes and Its Contribution to Volume Regulation. *Am. J. Physiol.—Cell Physiol.* 1998, 274 (2), C500-0512.

Notwithstanding the appended claims, the disclosure is also defined by the following clauses:

Clause 1. A composition comprising an amount of a meclofenamate derivative effective to modulate chloride ion channel (CLC) function.

Clause 2. The composition according to clause 1, wherein the meclofenamate derivative is described by formula (I):

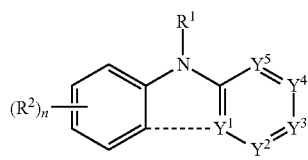

wherein:

--- is absent, or a bond;

$R^1$ is selected from hydrogen, alkyl, substituted alkyl, and -L-Z;

$R^2$ is selected from halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

$Y^1$ is selected from N and $CR^3$, wherein $R^3$ is selected from hydrogen, carboxyl, substituted carboxyl, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

or $Y^1$ is C when --- is a bond;

$Y^2$-$Y^5$ are each independently selected from N and $CR^3$, wherein $R^3$ is selected from hydrogen, carboxyl, substituted carboxyl, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label, and a fluorescent label; and n is an integer from 0 to 5, or a pharmaceutically acceptable salt or a solvate thereof.

Clause 3. The composition according to clause 1, wherein the meclofenamate derivative is described by formula (II):

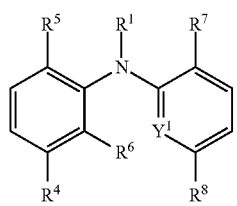

wherein:

$R^1$ is selected from hydrogen, alkyl, substituted alkyl, and -L-Z;

$R^4$ is selected from halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

$R^5$ and $R^6$ are each independently selected from halogen, alkyl, and substituted alkyl;

$Y^1$ is selected from N and CH;

$R^7$ is an anionic group;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label;

or a pharmaceutically acceptable salt or a solvate thereof.

Clause 4. The composition according to clause 3, wherein the anionic group is selected from a carboxylate, a phosphoryl, a sulfate, a tetrazole, and an amide.

Clause 5. The composition according to clause 1, wherein the meclofenamate derivative described by the formula (III):

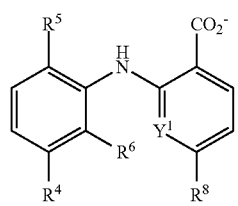

wherein:

$R^4$ is selected from alkyl, substituted alkyl, alkenyl, substituted alkenyl, alkynyl, substituted alkynyl, azide, hydroxyl, aryl, substituted aryl, cycloalkyl, substituted cycloalkyl, alkoxy, substituted alkoxy, and -L-Z;

$R^5$ and $R^6$ are each independently selected from halogen, alkyl, and substituted alkyl;

$Y^1$ is selected from N and CH;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label;

or a pharmaceutically acceptable salt or a solvate thereof.

Clause 6. The composition according to clause 1, wherein the meclofenamate derivative is a compound of FIG. 6.

Clause 7. The composition according to clause 1, wherein the meclofenamate derivative is a compound selected from:
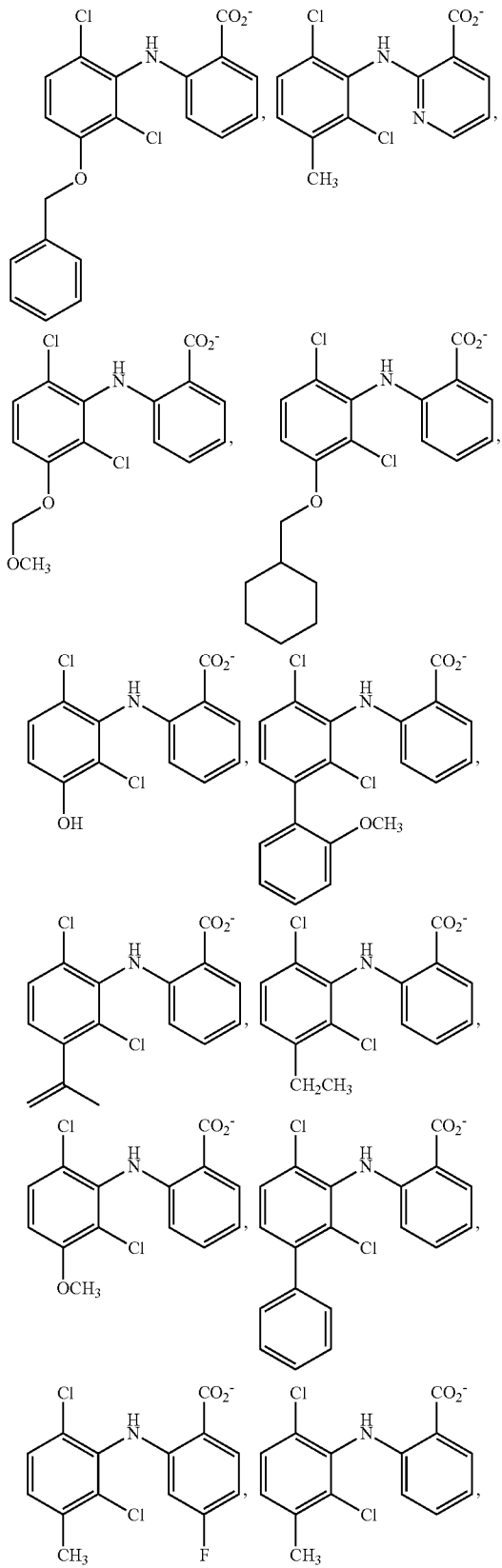
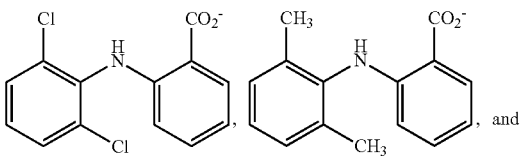
Clause 8. The composition according to clause 1, wherein the meclofenamate derivative is a compound selected from:
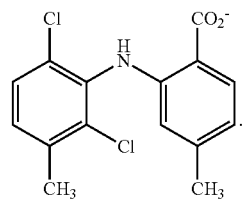
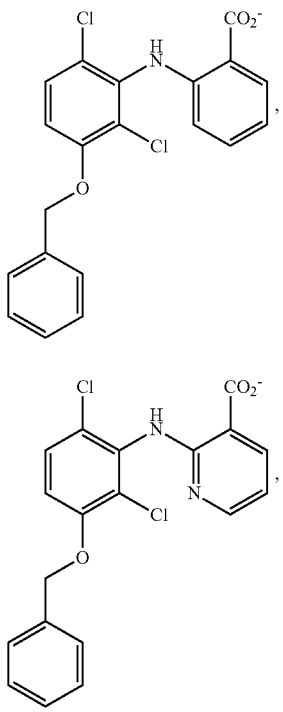
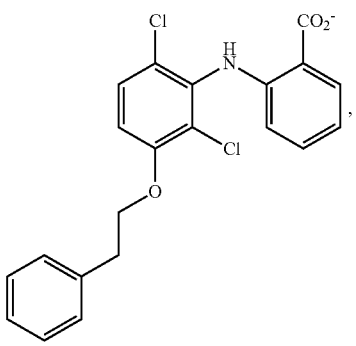

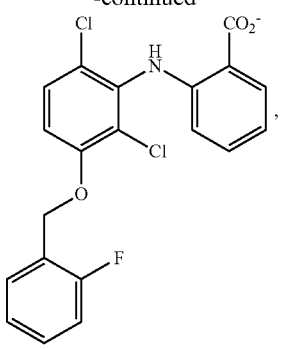
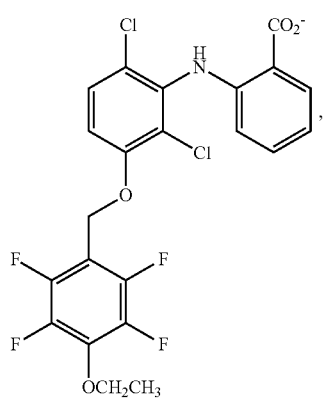
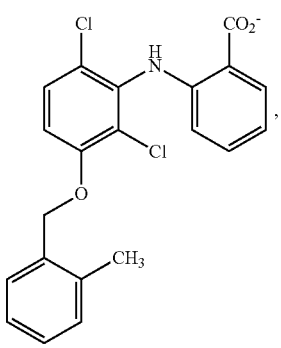
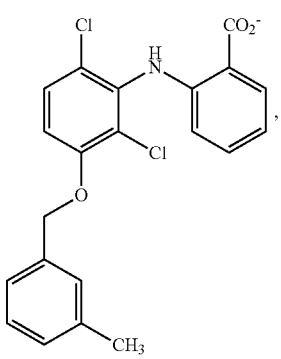
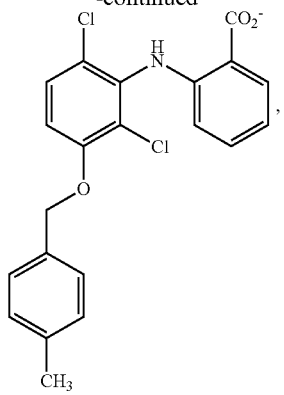
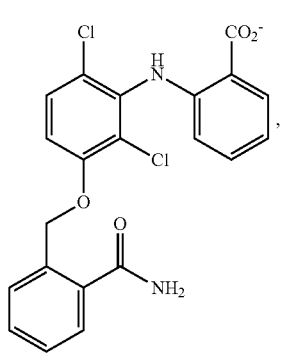
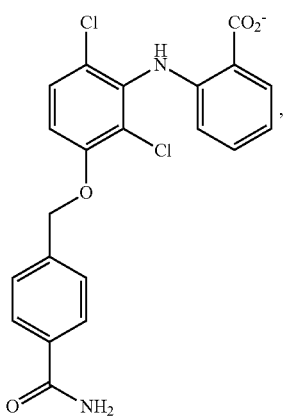
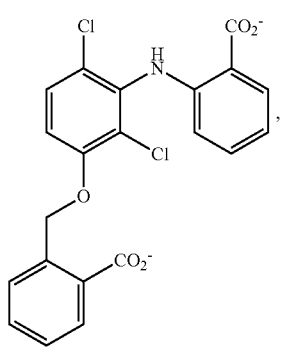

-continued

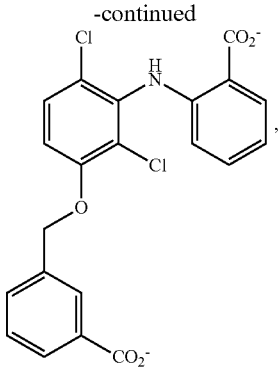

,

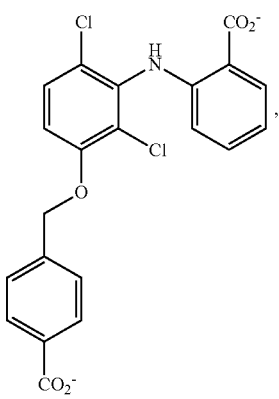

,

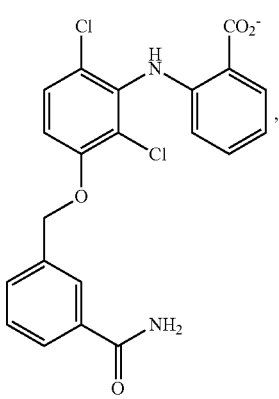

,

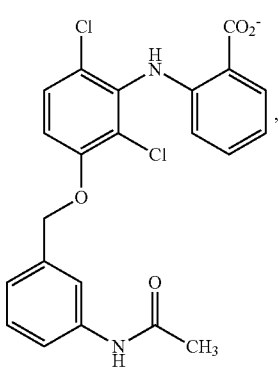

,

-continued

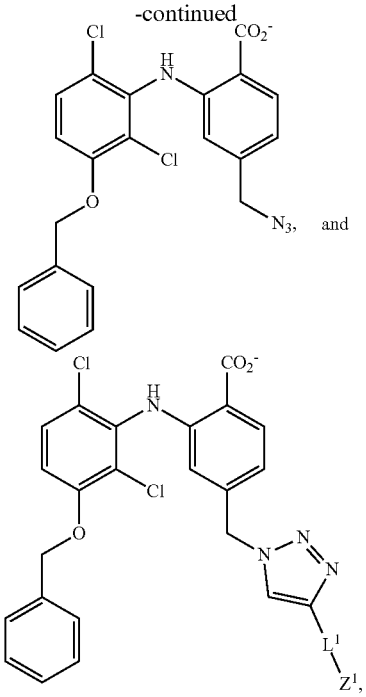

wherein:
L¹ is a PEG linker,
Z¹ is a biotin moiety.

Clause 9. The composition according to clause 1, wherein the CLC is CLC-2.

Clause 10. The composition according to clause 9, wherein the composition modulates CLC-2 function outside of a living organism.

Clause 11. The composition according to clause 9, wherein the composition modulates CLC-2 function in a living organism.

Clause 12. A method for modulating CLC-2 chloride channel activity in a subject suffering from a disorder associated with CLC-2 malfunction, comprising administering to the subject an effective amount of a meclofenamate derivative.

Clause 13. The method according to clause 12, wherein the meclofenamate derivative is described by formula (I):

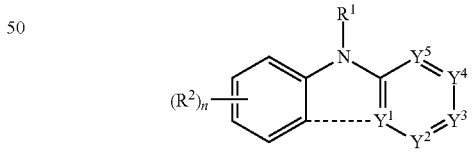

(I)

wherein:
--- is absent, or a bond;
R¹ is selected from hydrogen, alkyl, substituted alkyl, and -L-Z;
R² is selected from halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

$Y^1$ is selected from N and $CR^3$, wherein $R^3$ is selected from hydrogen, carboxyl, substituted carboxyl, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

or $Y^1$ is C when --- is a bond;

$Y^2$—$Y^5$ are each independently selected from N and $CR^3$, wherein $R^3$ is selected from hydrogen, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label; and n is an integer from 0 to 5, or a pharmaceutically acceptable salt or a solvate thereof.

Clause 14. The method according to clause 12, wherein the meclofenamate derivative is described by formula (II):

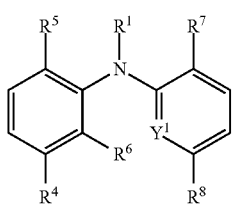

(II)

wherein:

$R^1$ is selected from hydrogen, alkyl, substituted alkyl, and -L-Z;

$R^4$ is selected from halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

$R^5$ and $R^6$ are each independently selected from halogen, alkyl, and substituted alkyl;

$Y^1$ is selected from N and CH;

$R^7$ is an anionic group;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label;

or a pharmaceutically acceptable salt or a solvate thereof.

Clause 15. The method according to clause 14, wherein the anionic group is selected from carboxylate, phosphoryl, sulfate, tetrazole, and amide.

Clause 16. The method according to clause 12, wherein the meclofenamate derivative described by the formula (III):

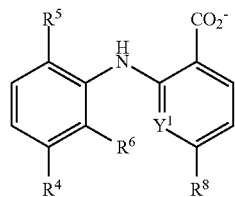

(III)

wherein:

$R^4$ is selected from alkyl, substituted alkyl, alkenyl, substituted alkenyl, alkynyl, substituted alkynyl, azide, hydroxyl, aryl, substituted aryl, cycloalkyl, substituted cycloalkyl, alkoxy, substituted alkoxy, and -L-Z;

$R^5$ and $R^6$ are each independently selected from halogen, alkyl, and substituted alkyl;

$Y^1$ is selected from N and CH;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label;

or a pharmaceutically acceptable salt or a solvate thereof.

Clause 17. The method according to clause 12, wherein the meclofenamate derivative is a compound of FIG. 6.

Clause 18. The method according to clause 12, wherein the meclofenamate derivative is a compound selected from:

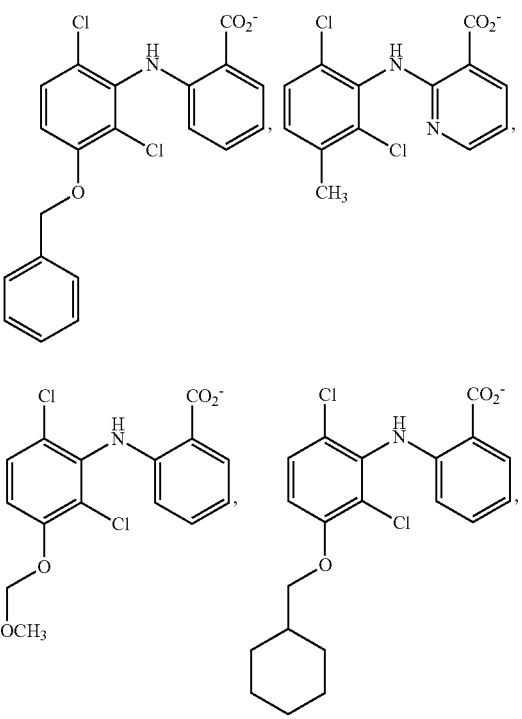

-continued
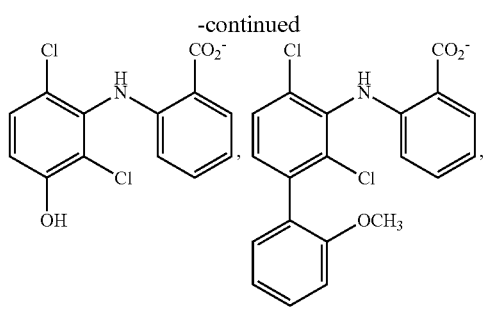
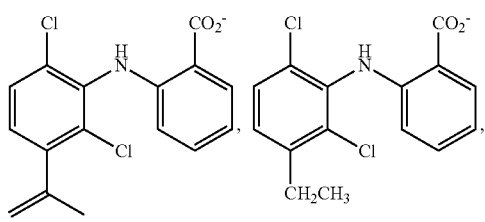
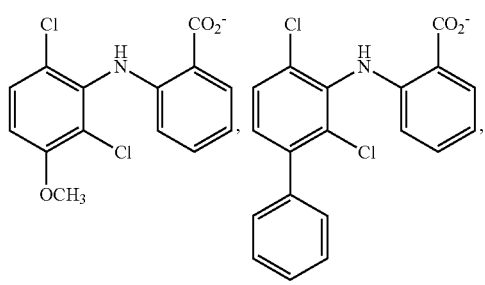
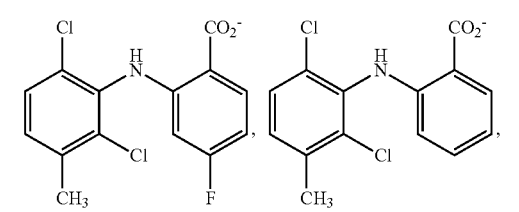
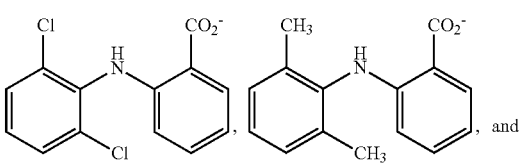, and
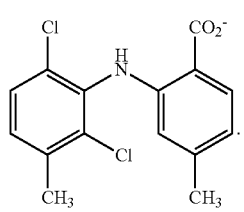.
Clause 19. The method according to clause 12, wherein the meclofenamate derivative is a compound selected from:
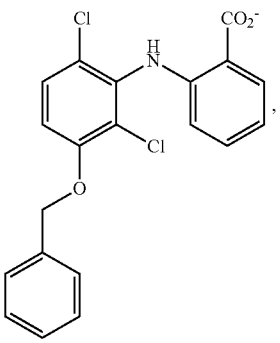,
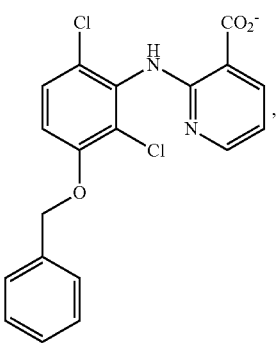,
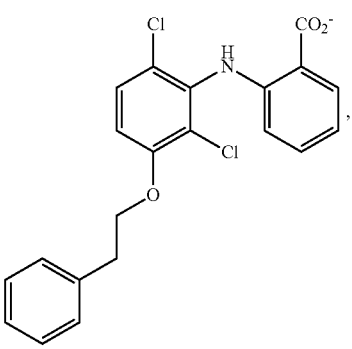,
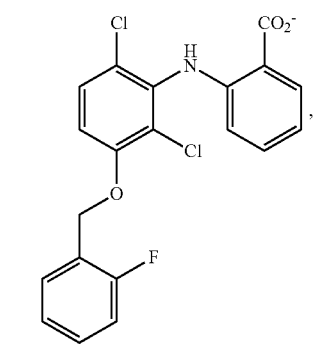,

67
-continued
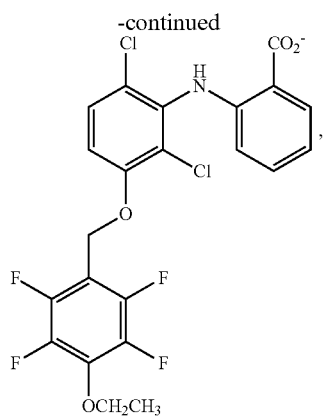
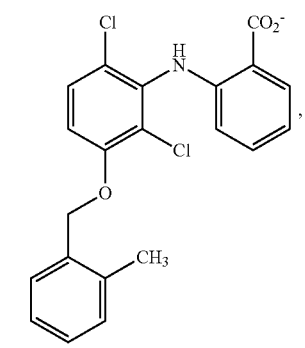
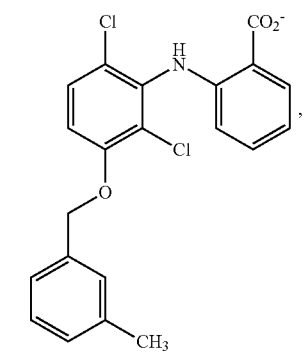
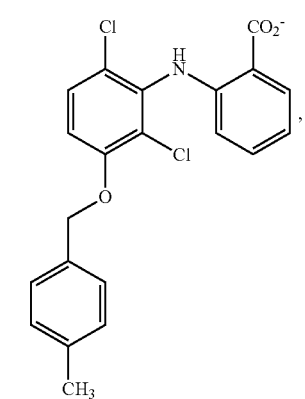
68
-continued
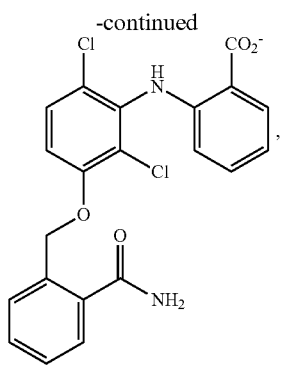
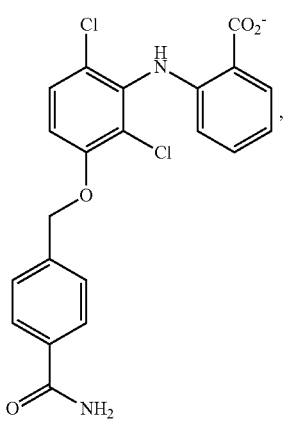
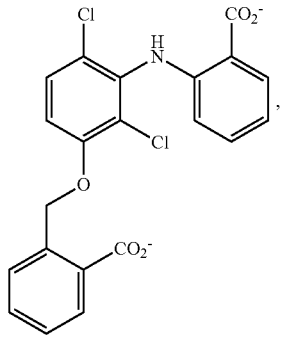
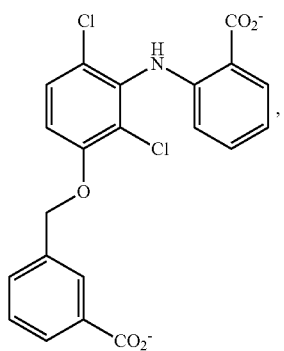

-continued

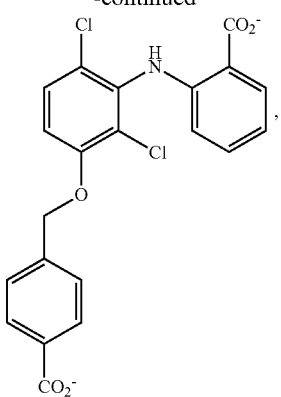

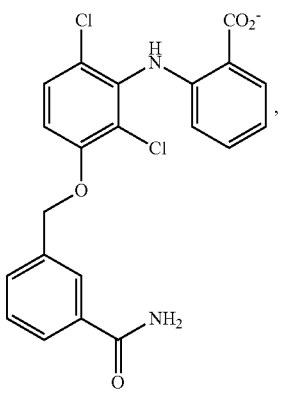

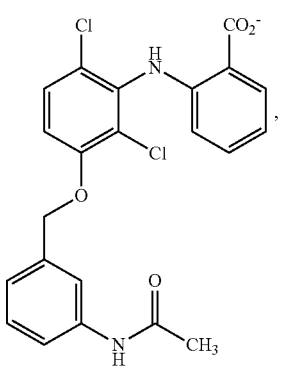

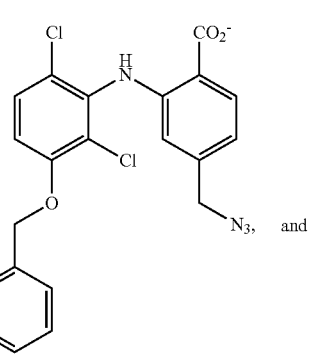

-continued

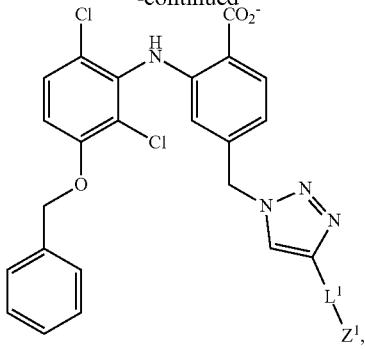

wherein:
L¹ is a PEG linker,
Z¹ is a biotin moiety.

Clause 20. The method of clause 12, wherein the disorder associated with CLC-2 malfunction is a disorder of the central nervous system (CNS).

Clause 21. The method of clause 20, wherein the disorder of the CNS is selected from epilepsy, leukoencephalopathy and gliomas.

Clause 22. A compound described by formula (II):

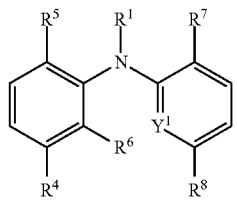

(II)

wherein:

$R^1$ is selected from hydrogen, alkyl, substituted alkyl, and -L-Z;

$R^4$ is selected from halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

$R^5$ and $R^6$ are each independently selected from halogen, alkyl, and substituted alkyl;

$Y^1$ is selected from N and CH;

$R^7$ is an anionic group;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label;

or a pharmaceutically acceptable salt or a solvate thereof, provided that the compound is not:

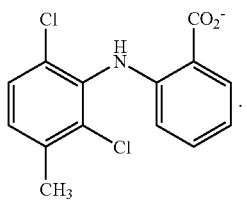

Clause 23. The compound according to clause 22, wherein the anionic group is selected from carboxylate, phosphoryl, sulfate, tetrazole, and amide.

Clause 24. The compound according to clause 22, described by the formula (III):

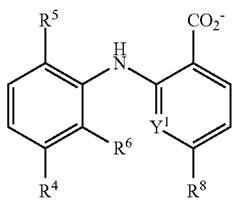

(III)

wherein:

$R^4$ is selected from alkyl, substituted alkyl, alkenyl, substituted alkenyl, alkynyl, substituted alkynyl, azide, hydroxyl, aryl, substituted aryl, cycloalkyl, substituted cycloalkyl, alkoxy, substituted alkoxy, and -L-Z;

$R^5$ and $R^6$ are each independently selected from halogen, alkyl, and substituted alkyl;

$Y^1$ is selected from N and CH;

$R^8$ is selected from hydrogen, halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;

L is an optional linker;

Z is selected from a chemoselective group, an affinity tag, an isotopic label and a fluorescent label;

or a or a pharmaceutically acceptable salt or a solvate thereof.

Clause 25. The compound according to clause 22, wherein $R^4$ is —O-benzyl.

Clause 26. The compound according to clause 22, wherein $R^5$ and $R^6$ are both chloride.

Clause 27. The compound according to clause 22, wherein $Y^1$ is CH.

Clause 28. The compound according to clause 22, wherein V is N.

Clause 29. The compound according to clause 22, wherein $R^8$ is -L-Z.

Clause 30. The compound according to clause 29, wherein Z comprises a biotin moiety.

Clause 31. The compound according to clause 22 selected from:

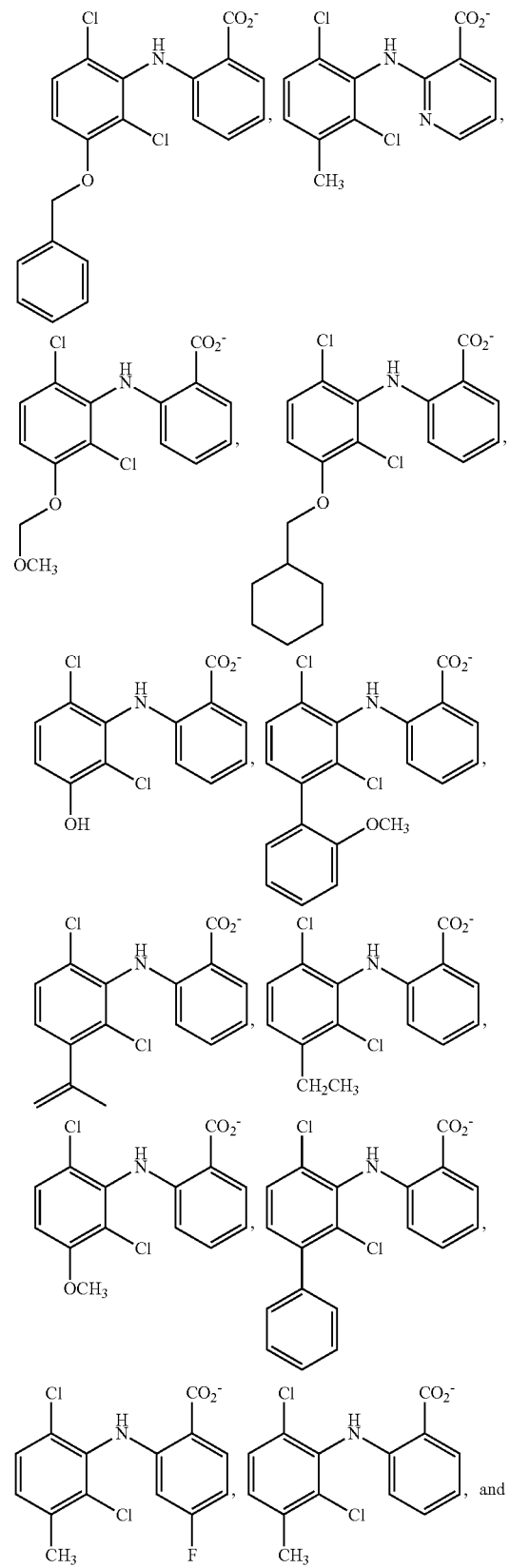

-continued
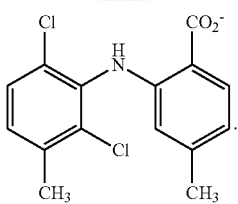
Clause 32. The compound according to clause 22 selected from:
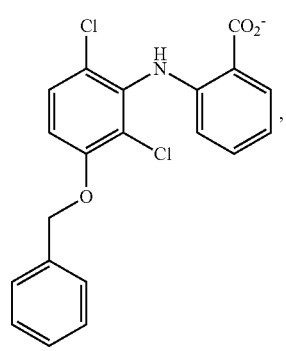
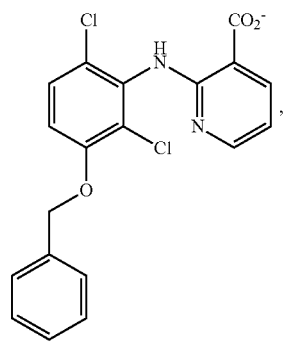
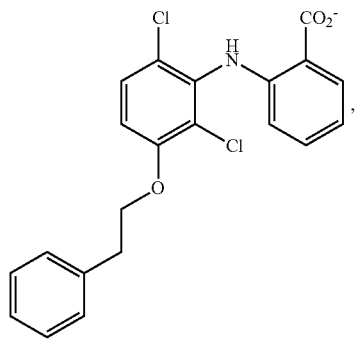
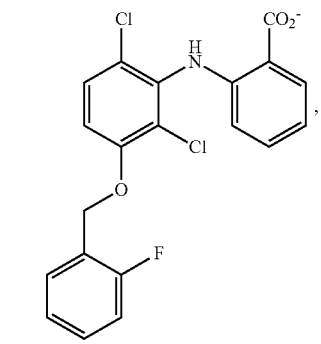
-continued
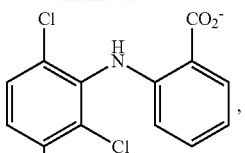
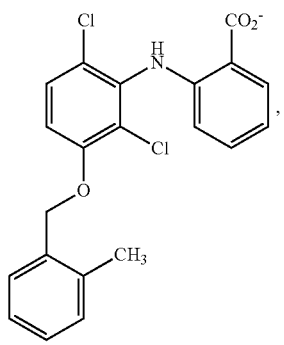
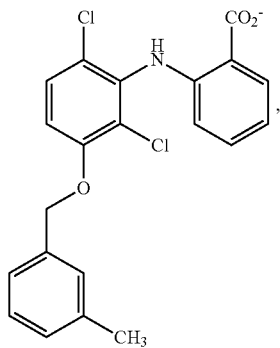
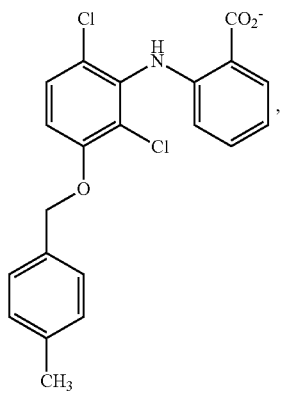

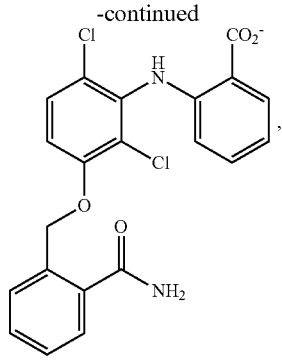
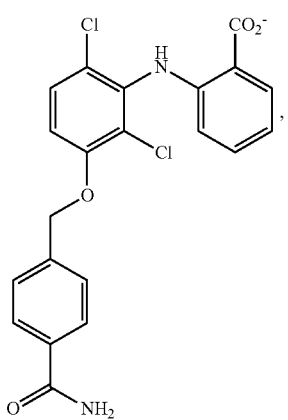
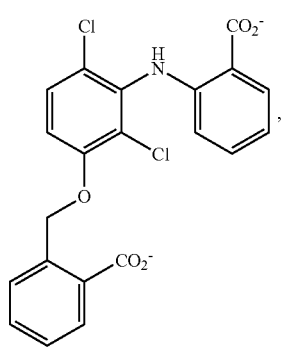
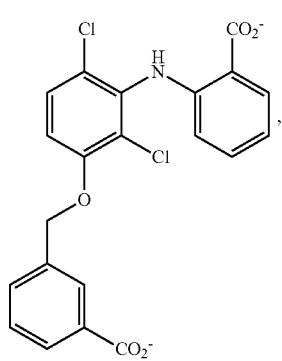
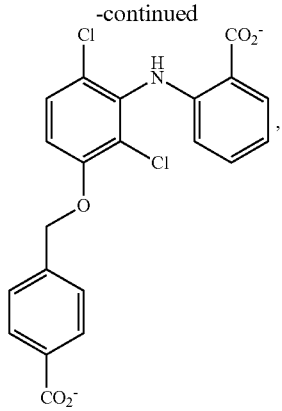
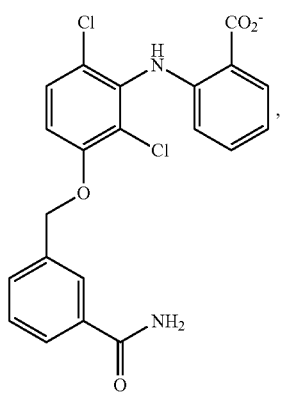
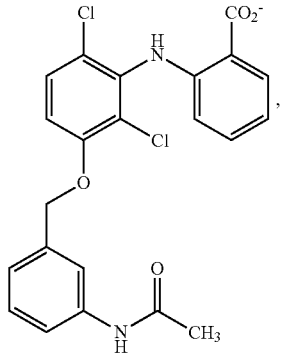
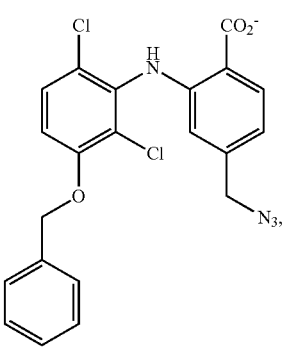

-continued

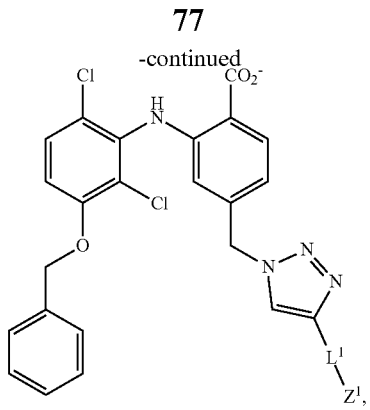

wherein:
$L^1$ is a PEG linker,
$Z^1$ is a biotin moiety.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A composition comprising an amount of a meclofenamate derivative effective to modulate chloride ion channel 2 (CLC2) function, wherein the meclofenamate derivative is described by formula (I):

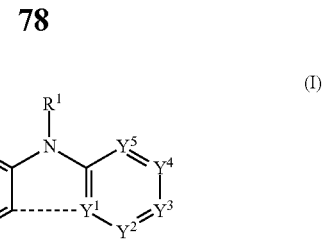

wherein:
is absent, or a bond;
$R^1$ is selected from hydrogen, alkyl, substituted alkyl, and -L-Z;
$R^2$ is selected from halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;
$Y^1$ is N;
or $Y^1$ is C when --- is a bond;
$Y^2$-$Y^5$ are each $CR^3$, wherein $R^3$ is selected from hydrogen, carboxyl, substituted carboxyl, an anionic group, halogen, alkyl, substituted alkyl, alkenyl, substituted alkenyl, alkynyl, substituted alkynyl, trifluoromethyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;
L is an optional linker;
Z is selected from a chemoselective group, an affinity tag, an isotopic label, and a fluorescent label; and
n is an integer from 0 to 5,
or a pharmaceutically acceptable salt or a solvate thereof.

2. The composition according to claim 1, wherein the meclofenamate derivative is described by formula (II):

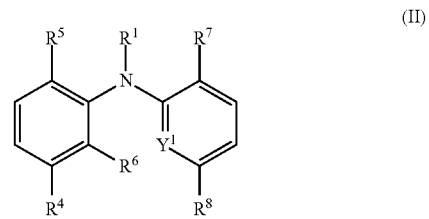

wherein:
$R^1$ is selected from hydrogen, alkyl, substituted alkyl, and -L-Z;
$R^4$ is selected from halogen, alkyl, substituted alkyl, alkenyl, substituted alkenyl, alkynyl, substituted alkynyl, azide, hydroxyl, aryl, substituted aryl, alkoxy, substituted alkoxy, cycloalkyl, substituted cycloalkyl, cycloalkene, substituted cycloalkene, heteroaryl, substituted heteroaryl, heterocycle, substituted heterocycle, and -L-Z;
$R^5$ and $R^6$ are each independently selected from halogen, alkyl, and substituted alkyl;
$Y^1$ is N;
$R^7$ is an anionic group selected from a carboxylate, a phosphoryl, a sulfate, a tetrazole, and an amide;

R[8] is hydrogen or L-Z;
L is an optional linker;
Z is selected from a chemoselective group, an affinity tag, an isotopic label and a fluorescent label;
or a pharmaceutically acceptable salt or a solvate thereof.

3. The composition according to claim 1, wherein the meclofenamate derivative is a compound selected from:

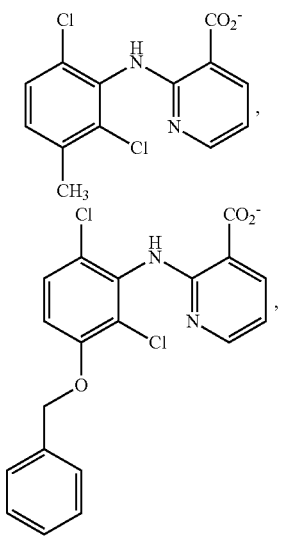

wherein:
L[1] is a PEG linker,
Z[1] is a biotin moiety.

4. The composition according to claim 1, wherein the composition modulates CLC-2 function outside of a living organism or in a living organism.

5. A composition comprising an amount of a meclofenamate derivative effective to modulate chloride ion channel 2 (CLC2) function, wherein the meclofenamate derivative is

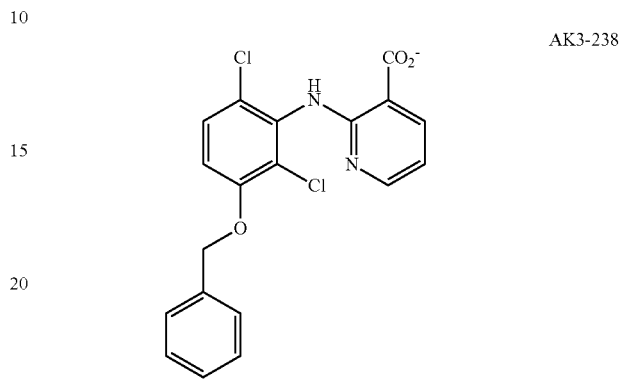

or a pharmaceutically acceptable salt or a solvate thereof.

6. The composition according to claim 5, wherein the composition modulates CLC-2 function outside of a living organism or in a living organism.

* * * * *